United States Patent
Kondyurin et al.

(10) Patent No.: US 7,597,924 B2
(45) Date of Patent: Oct. 6, 2009

(54) SURFACE MODIFICATION OF EPTFE AND IMPLANTS USING THE SAME

(75) Inventors: Alexey Kondyurin, Dresen (DE); Manfred Franz Maitz, Dresden (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 386 days.

(21) Appl. No.: 11/227,378

(22) Filed: Sep. 15, 2005

(65) Prior Publication Data

US 2007/0050007 A1    Mar. 1, 2007

Related U.S. Application Data

(60) Provisional application No. 60/709,257, filed on Aug. 18, 2005.

(51) Int. Cl.
  *B05D 3/06* (2006.01)
  *A61L 33/00* (2006.01)
  *H05H 1/00* (2006.01)
  *A61L 2/00* (2006.01)

(52) U.S. Cl. .................. 427/2.1; 427/2.24; 427/2.25; 427/533; 427/535; 427/536; 623/1.43; 623/1.46

(58) Field of Classification Search .............. 427/2.1, 427/2.24, 2.25, 533, 535, 536; 623/1.43, 623/1.46, 1.13
See application file for complete search history.

(56) References Cited

U.S. PATENT DOCUMENTS

| | | | |
|---|---|---|---|
| 4,661,383 A | 4/1987 | Elsenbaumer et al. | |
| 5,244,654 A | 9/1993 | Narayanan | |

(Continued)

FOREIGN PATENT DOCUMENTS

DE    199 04 913 A1    9/1999

(Continued)

OTHER PUBLICATIONS

Huang et al.; Surface modification of biomaterials by plasma immersion ion implantation; Surface & Coating Technology 186; pp. 218-226, 2004.

(Continued)

*Primary Examiner*—Timothy H Meeks
*Assistant Examiner*—Cachet I Sellman
(74) *Attorney, Agent, or Firm*—Vidas, Arrett & Steinkraus

(57) ABSTRACT

A method for modifying an ePTFE surface by plasma immersion ion implantation includes the steps of providing an ePTFE material in a chamber suitable for plasma treatment; providing a continuous low energy plasma discharge onto the sample; and applying negative high voltage pulses of short duration to form a high energy ion flux from the plasma discharge to generate ions which form free radials on the surface of the ePTFE material without changing the molecular and/or physical structure below the surface to define a modified ePTFE surface. The step of applying the high voltage pulses modifies the surface of the ePTFE without destroying the node and fibril structure of the ePTFE, even when the step of applying the high voltage pulses etches and/or carburizes the surface of the ePTFE. The modified surface may have a depth of about 30 nm to about 500 nm. The ions are dosed onto the ePTFE sample at concentrations or doses from about $10^{13}$ ions/cm$^2$ to about $10^{16}$ ions/cm$^2$.

42 Claims, 11 Drawing Sheets

U.S. PATENT DOCUMENTS

| | | | |
|---|---|---|---|
| 5,290,548 A | 3/1994 | Goldberg et al. | |
| 5,376,400 A | 12/1994 | Goldberg et al. | |
| 5,437,900 A | 8/1995 | Kuzowski | |
| 5,804,263 A | 9/1998 | Goldberg et al. | |
| 5,914,182 A | 6/1999 | Drumheller | |
| 6,022,902 A | 2/2000 | Koontz | |
| 6,306,165 B1 | 10/2001 | Pataik et al. | |
| 6,403,167 B1 * | 6/2002 | Lee et al. | 427/525 |
| 6,517,571 B1 * | 2/2003 | Brauker et al. | 623/1.13 |
| 6,632,470 B2 * | 10/2003 | Morra et al. | 427/2.24 |
| 6,780,497 B1 | 8/2004 | Walter | |
| 6,803,069 B2 | 10/2004 | Patnaik et al. | |
| 2001/0044655 A1 * | 11/2001 | Patnaik et al. | 623/1.43 |
| 2005/0003019 A1 | 1/2005 | Petersen | |
| 2005/0102025 A1 * | 5/2005 | Laroche et al. | 623/1.46 |
| 2005/0152813 A1 | 7/2005 | Noh | |

FOREIGN PATENT DOCUMENTS

| | | |
|---|---|---|
| EP | 0 930 331 A2 | 7/1999 |
| WO | WO 02/070032 A1 | 9/2002 |

OTHER PUBLICATIONS

Schiller et al.; Plasma immersion ion implantation of poly(tetrafluoroethylene); Surface and Coating Technology;177-178, pp. 483-488; 2004.

Tseng et al.; Effects of amide and amine plasma-treated ePTFE vascular grafts on endothelial cell lining in an artificial circulatory systems; Journal of Biomedical Materials Research; vol. 42, No. 1, pp. 188-198, Oct. 1998.

Takahashi et al.; Biocompatibility of ePTFE Modified by Ion Beam Irradiation; No Shinkei Geka vol. 32(4), pp. 339-344; 2004.

Yotoriyami et al.; Ion-Beam Irradiated ePTFE for the Therapy of Intracranial Aneurysms; No Shinkei Geka, vol. 32(5), pp. 471-478; 2004.

* cited by examiner

SURFACE MODIFICATION OF EPTFE AND IMPLANTS USING THE SAME

CROSS-REFERENCE TO RELATED APPLICATIONS

This application claims the benefit of U.S. Provisional Application No. 60/709,257, filed Aug. 18, 2005, the contents of which are incorporated herein by reference.

FIELD OF THE INVENTION

The present invention relates to surface modification of ePTFE and implants using the same. More particularly, the present invention relates to modification of ePTFE by plasma immersion ion implantation and fuctionalization of the modified ePTFE.

BACKGROUND OF THE INVENTION

An intraluminal prosthesis is a medical device used in the treatment of diseased bodily lumens. One type of intraluminal prosthesis used in the repair and/or treatment of diseases in various body vessels is a stent. A stent is a generally longitudinal tubular device formed of biocompatible material which is useful to open and support various lumens in the body. For example, stents may be used in the vascular system, urogenital tract, esophageal tract, tracheal/bronchial tubes and bile duct, as well as in a variety of other applications in the body. These devices are implanted within the vessel to open and/or reinforce collapsing or partially occluded sections of the lumen.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Tubular shaped structures, which have been used as intraluminal vascular stents, have included helically wound coils which may have undulations or zig-zags therein, slotted stents, ring stents, braided stents and open mesh wire stents, to name a few. Super-elastic materials and shape memory materials have been used to form stents.

A graft, including a shunt, for example, a dialysis shunt, is another commonly known type of intraluminal prosthesis which is used to repair, replace or bridge various body vessels. A graft provides a lumen through which fluids, such as blood, may flow. Moreover, a graft is often configured as being generally impermeable to blood to inhibit substantial leakage of blood therethrough. Grafts are typically hollow tubular devices that may be formed of a variety of materials, including textile and non-textile materials.

A stent and a graft may be combined into a stent-graft endoprosthesis to combine the features and advantages of each. For example, tubular coverings have been provided on the inner and/or outer surfaces of stents to form stent-grafts. It is often desirable to use a thin-walled graft or covering in the stent-graft endoprosthesis to minimize the profile of the endoprosthesis and to maximize the flow of blood through the endoprosthesis. In such cases non-textile materials, such as polymeric tubes or sheets formed into tubes, are often used.

Expanded polytetrafluoroethylene or e-PTFE is one common polymeric material used as the graft portion or covering of a stent-graft endoprosthesis.

Polytetrafluoroethylene (PTFE) is commonly used for implantable medical devices due to its chemical stability, bio-stability and bio-inertness. It is also highly hydrophobic. The mechanically stretched, expanded form (ePTFE) is microscopically porous and possesses the stability and inertness properties of PTFE. The hydrophobicity of PTFE and ePTFE and the low adsorption of proteins by PTFE and ePTFE were regarded as favourable characteristics for good performance in vascular vessels. Certain considerations, however, are present with implanted PTFE or ePTFE materials, including thrombosis and anastomosis stenosis by intima hyperplasia.

A thrombus is the formation of a solid body composed of elements of the blood, e.g., platelets, fibrin, red blood cells, and leukocytes. Thrombus formation is caused by blood coagulation and platelet adhesion to, and platelet activation on, foreign substances. When this occurs, a graft is occluded by such thrombotic material, which in turn, results in decreased patency for the graft. Accordingly, more stringent selection criteria are necessary for small caliber vascular graft materials because the small diameters of these grafts magnify the problem of deposition of such thrombotic material on the luminal surfaces of the graft.

Biologically designed PTFE or ePTFE surfaces, e.g. by heparin coating of the graft, can reduce platelet adherence and the intima proliferation. Heparin, however, has the problem of a physiological decay in biological activity and in some cases iatrogenic inactivation with protaminsulfate.

Endothelial cells as the inner lining of blood vessels are known to provide a hemocompatible surface. ePTFE as such, however, does not support endothelialization in vivo. Various attempts have been made to achieve an adherent layer of endothelial cells on the surface. Seeding the cells in a system with dynamic pressure and flow in vitro has been described as one way to obtain an endothelial lining, which resists the shear stress of physiological blood flow.

Some ways of surface modification of ePTFE, which influence polarity and surface energy, have been successfully attempted, such as surface treatment of ePTFE with energetic ions, either as plasma treatment or as ion beam irradiation of ePTFE. For example, amide and amine groups were deposited onto PTFE and ePTFE materials by radio frequency (RF) glow discharge plasma treatment of butylamine, and bovine aortic endothelial cells were then seeded on the amide/amine coated materials. See, Tseng et al., "Effects Of Amide And Amine Plasma-Treated ePTFE Vascular Grafts On Endothelial Cell Lining In An Artificial Circulatory System", Journal Of Biomedical Materials Research, 1998, Volume 42, pages 188-189. Such RF plasma treatment is typically done at low energy levels to deposit a thin coating, such as 30 to 100 Angstrom thick coating as reported in Tseng. While, improved cell adherence and proliferation for RF plasma treated ePTFE was reported as compared to the non-treated ePTFE, long term stability of the cell layer and the long term stability of the plasma treatment were not adequate because plasma treatment usually only has a relatively short term effect as the modified molecules tend to migrate into the bulk of the polymer. Ion beam irradiation has been used to modify the surface of ePTFE. See, Yotoriyama et al., Ion-Beam Irradiated ePTFE For The Therapy Of Intracranial Aneurysms", No Shinkei Geka 2004, 32, pages 471-478; Takahashi et al, "Biocompatibility Of ePTFE Modified By Ion Beam Irradiation", No Shinkei Geka 2004, 32, pages 339-344. Yotoriyama and Takahashi report improved cell adhesion to the irradiated ePTFE surfaces. The surfaces were irradiated with argon, helium, krypton and neon ions by ion beam techniques with high ion energy levels of 150 keV. Such high energy levels, however, were reported in Yotoriyama to destroy the fibrils of the ePTFE.

Thus, there is a need in the art for modifying the surface of ePTFE to promote cell adhesion without the disadvantages of the prior art. In particular, there is the need for modifying the surface of ePTFE to promote cell adhesion without destroying the node and fibril structure of the ePTFE.

SUMMARY OF THE INVENTION

In one aspect of the present invention, a method for modifying an ePTFE surface by plasma immersion ion implantation includes the steps of providing an ePTFE material on a sample holder in a chamber suitable for plasma treatment; providing a continuous low energy plasma discharge onto the sample; and applying short negative high voltage pulses of short duration to the sample holder to form a high energy ion flux from the plasma discharge and directed to the ePTFE material. The free radials generated on the surface of the ePTFE material without changing the molecular and/or physical structure below the surface to define a modified ePTFE surface. The ePTFE material has a node and fibril structure, and the step of applying the high voltage pulses modifies the surface of the ePTFE without destroying the node and fibril structure, even when the step of applying the high voltage pulses etches and/or carburizes the surface of the ePTFE. The modified surface may have a depth of about 30 nm to about 500 nm. Desirably, the ions are dosed onto the ePTFE sample at concentrations or doses from about $10^{13}$ ions/cm to about $10^{16}$ ions/cm$^2$.

The step of providing the continuous low energy plasma discharge onto the sample may further include the step of generating the plasma discharge at a radiofrequency of about 13.56 MHz or about 2.45 GHz. These radiofrequencies are non-limiting, and other radiofrequencies may suitably be used. The step of providing the continuous low energy plasma discharge onto the sample, may also further include the step of providing a source of gas from which the plasma is generated, wherein the gas is selected from the group consisting of nitrogen, oxygen, argon and combinations thereof.

The step of applying high voltage pulses for a short period of time to form an ion flux from the plasma discharge may further include the step of applying voltages from about −0.5 kV to about −40 kV. The step of applying high voltage pulses for a short period of time to form an ion flux from the plasma discharge may also further include the step of applying voltages from about −0.5 kV to about −20 kV. The step of applying high voltage pulses for a short period of time to form an ion flux from the plasma discharge may also further include the step of applying voltages at a frequency from 0.2 Hz to 200 Hz. The voltages may be applied for a duration of about 1 to about 10 microseconds, desirably for a duration of about 5 microseconds.

The power to generate the plasma discharge according to the present invention may vary from 50 watts to 500 watts. The pressure within the chamber may be reduced to a pressure of about 0.1 Pa to about 1.0 Pa.

The method for modifying ePTFE surfaces may further include the step or steps of oxidizing at least a portion of the free radials; functionalizing the free radical sites with a spacer molecule or material, wherein the spacer molecule or material may be covalently bonded to the ePTFE; functionalizing the free radical sites with hydrophilic acrylamide groups; covalently bonding the hydrophilic acrylamide groups to the modified ePTFE surface; functionalizing the free radical sites with polysaccharide hydroxyethyl starch groups; covalently bonding the polysaccharide hydroxyethyl starch groups to the modified ePTFE surface; covalently bonding a bioactive agent bonded to the modified ePTFE surface; covalently bonding a bioactive agent bonded to the hydrophilic acrylamide groups that are covalently bonded to the modified ePTFE surface; covalently bonding a bioactive agent bonded to the polysaccharide hydroxyethyl starch groups that are covalently bonded to the modified ePTFE surface; and combinations thereof. Useful bioactive agents include anti-thrombogenic agents (such as heparin, heparin derivatives, hirudin, acetylsalicylic acid, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; agents which interfere with endogenous vasoactive mechanisms; adhesion factors (such as RGD sequence containing compounds, lysine, poly-L-lysine, antibodies against endothelial cell markers and/or their precursor cells/stem cells, and elastin); and combinations thereof.

The ePTFE sample modified by the methods of the present invention may be an implantable medical device, for example a vascular or non-vascular device. Useful devices include, without limitition, a vascular or non-vascular graft or shunt, a vascular or non-vascular stent, a vascular or non-vascular stent-graft, a patch, such as a patch useful in herniorraphy or craniosurgery, a material or sheet for dura replacement, and the like.

In another aspect of the present invention, an implantable medical device is provided. The device includes ePTFE having a surface modified by plasma immersion ion implantation; and polysaccharide hydroxyethyl starch groups covalently bonded to the modified surface. The implantable medical device may further include a bioactive agent bonded to the polysaccharide hydroxyethyl starch groups. Useful bioactive agents include anti-thrombogenic agents (such as heparin, heparin derivatives, hirudin, acetylsalicylic acid, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/ antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; agents which interfere with endogenous vasoactive mechanisms; adhesion factors (such as RGD sequence containing compounds, lysine, poly-L-lysine, antibodies against endothelial cell markers and/or their precursor cells/stem cells, and elastin); and combinations thereof. The implantable medical device may be a graft, including a vascular graft, or a stent-graft, including a vascular stent-graft.

In another aspect of the present invention, an implantable medical device is provided in which the device includes ePTFE having a surface modified by plasma immersion ion implantation; and hydrophilic acrylamide groups covalently bonded to the modified surface. The implantable medical device may further include a bioactive agent bonded, such as one or more of the above-described agents, to the hydrophilic acrylamide groups. The implantable medical device may be a vascular or non-vascular graft or shunt, a vascular or non-vascular stent, a vascular or non-vascular stent-graft, a patch, such as a patch useful in hemiorrphy or craniosurgery, a material or sheet for dura replacement, and the like.

In another aspect of the present invention, an implanted, surface modified ePTFE graft includes ePTFE having a node and fibril structure and having a carburized surface formed by plasma immersion ion implantation without destroying the node and fibril structure and having cellular material attached to the fibrils or attached to functional groups covalently bonded to the fibrils and substantially covering and/or filling the nodes. The carburized surface desirably has a depth of about 30 nm to about 500 nm.

In another aspect of the present invention a surface modified ePTFE includes ePTFE having a node and fibril structure and having a carburized surface formed by plasma immersion ion implantation without destroying the node and fibril structure and having seed cells and/or protein material attached to the fibrils and/or attached to spacer groups, preferably hydrophilic acrylamide groups and/or polysaccharide hydroxyethyl starch groups, covalently bonded to the fibril. Useful, but non-limiting, seed cells include epithelial cells (e.g., keratinocytes, hepatocytes), neurons, glial cells, astrocytes, podocytes, mammary epithelial cells, islet cells, endothelial cells (e.g., aortic, capillary and vein endothelial cells), and mesenchymal cells (e.g., adipocytes, dermal fibroblasts, mesothelial cells, osteoblasts), smooth muscle cells, striated muscle cells, ligament fibroblasts, tendon fibroblasts, adult fibroblasts, fibrocytes, chondrocytes, osteocytes, stem cells, genetically modified cells, immunologically masked cells, combinations thereof, and the like. Useful protein material includes fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, kalinin, combinations thereof and the like. Such materials may be useful as a scaffold for seeding cells, i.e., in vitro tissue engineering. The carburized surface desirably has a depth of about 30 nm to about 500 nm.

DETAILED DESCRIPTION OF THE PREFERRED EMBODIMENT

Figure 1:
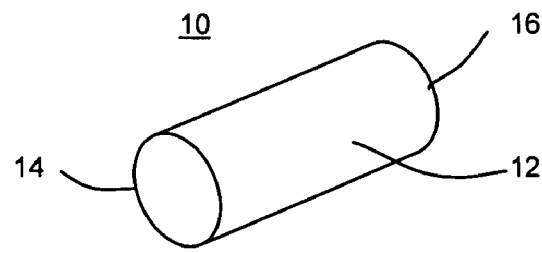
FIG. 1 is a perspective view of a graft according to the present invention.

The present invention is directed to ion implantation into ePTFE by plasma immersion ion implantation (PIII) of nitrogen, oxygen and/or argon ions and a subsequent chemical functionalization of the surface.

Plasma immersion ion implantation modifies the surface modification of a polymer, such as ePTFE, by the penetration of high energy ions into the polymer, cascades of collisions with atoms of macromolecules and the transfer of the kinetic energy of the penetrating ion to atoms and electrons of the polymer macromolecules. The transferred energy is high enough to break chemical bondings in the macromolecule and released atoms and electrons fly with high kinetic energy causing new collisions with nearest macromolecules. As result, chemical breaking of chemical bondings, ionization, formation of free radicals, electron and phonon excitation of macromolecules occur. The area of such strong structural changes of polymer is named an ion track and the size of an ion track depends on ion energy, kind of ion and polymer. These reactions occur in the first stage of the ion beam implantation into polymers during $10^{-9}$ to $10^{-6}$ seconds.

After ion penetration, the track field of polymer has a very high concentration of free radicals, ionized and highly excited parts of macromolecules, which induce a number of chemical reactions in this destructed field of polymer. The products are amorphous carbon, aromatic condensed structures, stable and semi-stable free radical structures. The free radicals cause chain reactions of hydrogen breaking from initial macromolecules and the modifications range significantly deeper than the track of ions. As used herein the term "carburizing" and variants thereof refers to the formation of amorphous carbon, aromatic condensed structures, stable and semi-stable free radical structures into a polymer surface, such as ePTFE. The duration of the second stage is much longer than the first stage of structure transformations. The properties of polymer surface after ion beam implantation are mostly related to this second stage. During the second structure transformation stage in presence of air the free radical reactions of the modified polymer layer are involve atmospheric oxygen and stable oxygen-containing groups appear in the polymer. These structure transformations in polymer surface layer can be used for different applications including medical devices. Desirably, the carburized surface has a depth of about 30 nm to about 500 nm, more desirably from about 50 nm to 150 nm, preferably about 100 nm.

In plasma immersion ion implantation, a sample, such as a polymeric sample, for example ePTFE, is placed on a holder in continuous low energy plasma discharge and high voltage pulses are applied for a short time for the formation of an ion flux from the plasma cloud.

While polymer surfaces have been functionalized by plasma treatment. In contrast to plasma immersion ion implantation, plasma treatment usually only has a relatively short term effect, because the modified molecules tend to migrate into the bulk of the polymer. With plasma immersion ion implantation, however, the polymer, for example ePTFE is treated with higher energetic ions, which induce carburization of the surface. Carburization of the polymeric surface prevents this surface from remodelling, i.e., migration into the polymer bulk.

Ion implantation by plasma immersion ion implantation into polymers may lead to the formation of dangling bondings and free radicals in the polymer surface. Such free radicals are potentially toxic for adherent cells, even though no such effect was with the methods of the present invention as described in the examples below. To reduce the potential toxic effects, these bondings may be saturated prior to implantation of the ePTFE into a bodily lumen of a patient. In one aspect of the present invention, these bondings may be saturated with the highly hydrophilic acrylamide. Useful acrylamides have the structure of

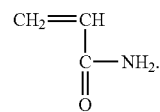

The highly hydrophilic acrylamide covalently bonds to the polymer surface and, due to chemical reaction with active groups on the polymer surface, polyacrylamide forms, as follows:

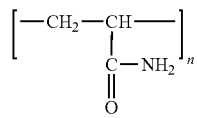

Free monomers of toxic substances, if any, may then be washed out.

Alternatively to acrylamide, modified polysaccharide hydroxyethyl starch (HAES) may be used to saturate the free radicals on the polymer surface. A useful modified polysaccharide hydroxyethyl starch includes those materials having the structural formula of

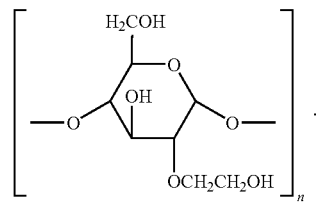

Useful modified polysaccharide hydroxyethyl starches include those having an average non-limiting molecular weight of about 200 and substitution rate from about 0.40 to about 0.55, desirably about 0.5. Desirably, the HAES may have a molecular weight from about 150 to about 300, preferably about 200. HAES has been used in clinical application as plasma expanders for the treatment of hypovolaemia and shock. Due to the substitution, the HAES is more soluble in water than ordinary starches and more resistant against degradation. In solution it tends to inhibit haemostatic processes by interaction with clotting factors and blood platelets. Endothelial cells also internalize the free form by pinocytosis and eliminate only about 50% of it. The expression of activation markers is not modulated by this, but HAES directly inhibits the interaction with polymorphonuclear neutrophils.

A method for modifying an ePTFE surface by plasma immersion ion implantation according to the present invention includes the steps of providing an ePTFE material in a chamber suitable for plasma treatment; providing a continuous low energy plasma discharge onto the sample; and applying high voltage pulses for a short period of time to form a high energy ion flux from the plasma discharge to generate ions which form free radials on the surface of the ePTFE material without changing the molecular and/or physical structure below the surface to define a modified ePTFE surface. The step of applying the high voltage pulses is controlled to modify the surface of the ePTFE without destroying the node and fibril structure of the ePTFE. The energy and frequency of the voltage pulses are also controlled to etch and/or carburize the surface of the ePTFE without destroying the node and fibril structure. The continuous low energy plasma discharge is provided by generating the plasma discharge at a radiofrequency of about 13.56 MHz or about 2.45 GHz. These radiofrequencies are non-limiting, and other radiofrequencies may suitably be used. The source of gas from which the plasma is generated may include nitrogen, oxygen, argon and combinations thereof. Desirably, these gaseous ions are used in the methods of the present invention to carburize the surface of the ePTFE as compared to prior art methods where mere coatings of molecules were deposited onto ePTFE surfaces.

Short term high voltage pulses from about −0.5 kV to about −40 kV are applied to the sample or the sample holder to accelerate ions from the plasma toward the sample. Voltages from about −0.5 kV to about −30 kV, from about −0.5 kV to about −20 kV, from about −5 kV to about −40 kV, from about −10 kV to about −30 kV, and from about −20 kV to about −30 kV are also useful. The voltages may be applied at a frequency from about 0.2 Hz to about 200 Hz. The voltages may also be applied for a duration of about 1 to about 10 microseconds, desirably about 5 microseconds.

Power to generate to the plasma discharge was from about 50 watts to about 500 watts, desirably from about 50 to about 400 watts. With plasma immersion ion implantation, the chamber operates at a reduced, but non-limiting, pressure of about 0.1 to about 1.0 Pa. Desirably, ions are dosed onto the ePTFE surface at about $10^{13}$ to about $10^{16}$ ions/cm$^2$.

Such methods carburize the ePTFE surface. After carburization of the ePTFE surface, the free radicals on the ePTFE, or a portion of the free radicals on the ePTFE surface, are desirably oxidized by exposing the ePTFE material to an oxidizing environment, for example exposure to air.

The free radial sites or the oxidized free radical sites may be functionalized with a spacer molecule or material. In contrast to the coating methods of the prior art, the spacer molecule or material is covalently bonded to the ePTFE. Useful, but non-limiting, examples of spacer molecules or materials include the above-described hydrophilic acrylamide groups, polysaccharide hydroxyethyl starch groups and combinations thereof.

Moreover, a bioactive agent may be covalently bonded to the modified ePTFE surface or to the spacer molecules, i.e., hydrophilic acrylamide groups, polysaccharide hydroxyethyl starch groups and combinations thereof. Useful, but non-limiting, bioactive agents include anti-thrombogenic agents (such as heparin, heparin derivatives, hirudin, acetylsalicylic acid, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; agents which interfere with endogenous vasoactive mechanisms; adhesion factors (such as RGD sequence containing compounds, lysine, poly-L-lysine, antibodies against endothelial cell markers and/or their precursor cells/stem cells, and elastin); and combinations thereof.

The modified and/or functionalized ePTFE materials 12 of the present invention are useful as an implantable medical device, for example, vascular graft 10, which is depicted in FIG. 1. Graft 10 is an ePTFE or PTFE containing graft. As depicted in FIG. 1, graft 10 is a hollow tubular structure having opposed open ends 14, 16. The present invention, however, is not limited to a single lumen tubular graft. For example, grafts of the present invention may have branches, for example a bifurcated graft, or a varied shaped, for example flared or varying diameter, wall portion.

Figure 2:
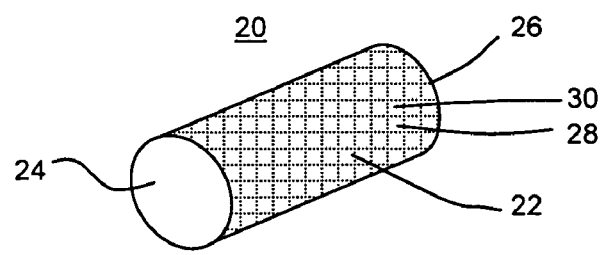
FIG. 2 is a perspective view of a stent-graft according to the present invention.

As depicted in FIG. 2, functionalized ePTFE materials 22 of the present invention are useful as an implantable medical device, for example, stent-graft 20. Stent-graft 20 includes functionalized ePTFE material 22, which may be in the form of a graft covering or otherwise disposed over a stent 28. Typically, the stent-graft 20 is a hollow tubular device having opposed open ends 24, 26. The stent 28 includes elongate members 30, such as wire strands formed into a hollow tubular structure.

Desirably, the elongate strands or wires 30 are made from nitinol, stainless steel, cobalt-based alloy such as Elgiloy, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly (L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly (phosphazene) poly(D,L-lactide-co-caprolactone) PLA/PCL), poly(glycolide-co-caprolactone) (PGA/PCL), poly (phosphate ester) and the like. Wires made from polymeric materials may also include radiopaque materials, such as metallic-based powders, particulates or pastes which may be incorporated into the polymeric material. For example the radiopaque material may be blended with the polymer composition from which the polymeric wire is formed, and subsequently fashioned into the stent as described herein. Alternatively, the radiopaque material may be applied to the surface of the metal or polymer stent. In either embodiment, various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626, 936, which is herein incorporated in its entirely by reference. Metallic complexes useful as radiopaque materials are also contemplated. The stent may be selectively made radiopaque at desired areas along the wire or made be fully radiopaque, depending on the desired end-product and application. Further, the wires 30 have an inner core of tantalum, gold, platinum, iridium or combination of thereof and an outer member or layer of nitinol to provide a composite wire for improved radiocapicity or visibility. Desirably, the inner core is platinum and the outer layer is nitinol. More desirably, the inner core of platinum represents about at least 10% of the wire based on the overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Patent Application Publication 2002/0035396 A1, the contents of which is incorporated herein by reference.

Various stent types and stent constructions may be employed in the invention as the stent 20. Among the various stents useful include, without limitation, self-expanding stents and balloon expandable extents. The stents may be capable of radially contracting, as well and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents. The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like. Examples of various stent configurations are shown in U.S. Pat. No. 4,503,569 to Dotter; U.S. Pat. No. 4,733,665 to Palmaz; U.S. Pat. No. 4,856,561 to Hillstead; U.S. Pat. No. 4,580,568 to Gianturco; U.S. Pat. No. 4,732,152 to Wallsten, U.S. Pat. No. 4,886,062 to Wiktor, and U.S. Pat. No. 5,876,448 to Thompson, all of whose contents are incorporated herein by reference.

Figure 3:
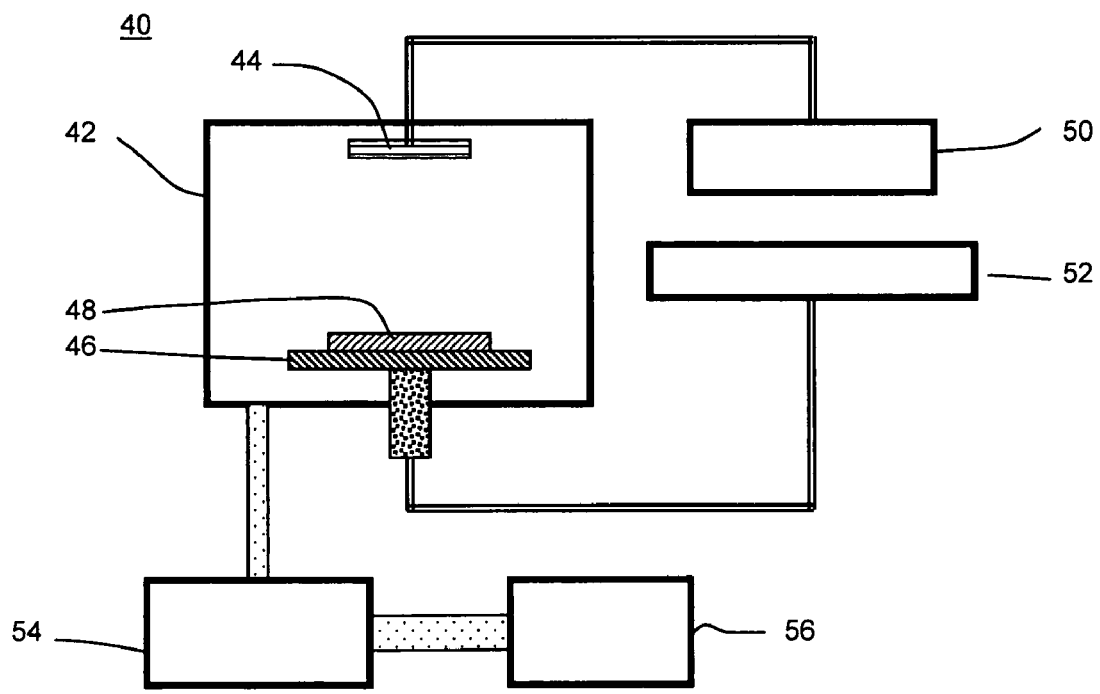
FIG. 3 is a schematic depiction of a system for plasma immersion ion implantation according to the present invention.

A system 40 for immersion ion implantation of samples, such as PTFE or ePTFE samples, is depicted in FIG. 3. The system 40 includes a chamber 42, a radiofrequency antenna 44, a high voltage electrode 46, a sample holder 48, a plasma generator 50, a high voltage generator 52, a turbo-molecular pump 54 and a vacuum pump 56, interrelated as shown. A sample (not shown) may be placed on or otherwise secured to the sample holder 48. The turbo-molecular pump 54 and the vacuum pump 56 are useful for controlling the pressure and flow of gas within the chamber 42. The plasma generator 50 and the radiofrequency antenna 44 are useful for generating a continuous low plasma discharge (not shown). The high voltage electrode 46 and the high voltage generator 52 are useful for generating and applying high voltage pulses of short duration to form a high energy ion flux from the plasma discharge to generate ion capable of forming free radials on the surface of the sample, i.e., high energy ions.

In one aspect of the present invention, a method for modifying an ePTFE surface by plasma immersion ion implantation includes the steps of providing an ePTFE material in a chamber suitable for plasma treatment; providing a continuous low energy plasma discharge onto the sample; and applying high voltage pulses for a short period of time to form a high energy ion flux from the plasma discharge to generate ions which form free radials on the surface of the ePTFE material without changing the molecular and/or physical structure below the surface to define a modified ePTFE surface. The ePTFE material has a node and fibril structure, and the step of applying the high voltage pulses modifies the surface of the ePTFE without destroying the node and fibril structure, even when the step of applying the high voltage pulses etches and/or carburizes the surface of the ePTFE. The modified surface may have a depth of about 30 nm to about 500 nm. Desirably, the ions are dosed onto the ePTFE sample at concentrations or doses from about $10^{13}$ ions/cm$^2$ to about $10^{16}$ ions/cm$^2$.

The step of providing the continuous low energy plasma discharge onto the sample may further include the step of generating the plasma discharge at a radiofrequency of about 13.56 MHz or about 2.45 GHz. Such useful radiofrequencies are non-limiting and other radiofrequencies may suitably be used. The step of providing the continuous low energy plasma discharge onto the sample, may also further include the step of providing a source of gas from which the plasma is generated, wherein the gas is selected from the group consisting of nitrogen, oxygen, argon and combinations thereof.

The step of applying high voltage pulses for a short period of time to form an ion flux from the plasma discharge may further include the step of applying voltages from about −0.5 kV to about −40 kV. The step of applying high voltage pulses for a short period of time to form an ion flux from the plasma discharge may also further include the step of applying voltages from −0.5 kV to −20 kV. The step of applying high voltage pulses for a short period of time to form an ion flux from the plasma discharge may also further include the step of applying voltages at a frequency from 0.2 Hz to 200 Hz. The voltages may be applied for a duration of about 1 to about 10 microseconds, desirably for a duration of about 5 microseconds.

The power to generate the plasma discharge according to the present invention may vary from 50 watts to 500 watts. The pressure within the chamber may be reduced to a pressure of about 0.1 Pa to about 1.0 Pa.

The method for modifying ePTFE surfaces may further include the step or steps of oxidizing at least a portion of the free radials; functionalizing the free radical sites with a spacer molecule or material, wherein the spacer molecule or material is covalently bonded to the ePTFE; functionalizing the free radical sites with hydrophilic acrylamide groups; covalently bonding the hydrophilic acrylamide groups to the modified ePTFE surface; functionalizing the free radical sites with polysaccharide hydroxyethyl starch groups; covalently bonding the polysaccharide hydroxyethyl starch groups to the modified ePTFE surface; covalently bonding a bioactive agent bonded to the modified ePTFE surface; covalently bonding a bioactive agent bonded to the hydrophilic acrylamide groups that are covalently bonded to the modified ePTFE surface; covalently bonding a bioactive agent bonded to the polysaccharide hydroxyethyl starch groups that are covalently bonded to the modified ePTFE surface; and combinations thereof. Useful bioactive agents include anti-thrombogenic agents (such as heparin, heparin derivatives, hirudin, acetylsalicylic acid, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; agents which interfere with endogenous vasoactive mechanisms; adhesion factors (such as RGD sequence containing compounds, lysine, poly-L-lysine, antibodies against endothelial cell markers and/or their precursor cells/stem cells, and elastin); and combinations thereof.

The ePTFE sample modified by the methods of the present invention may be an implantable medical device, for example, a vascular or non-vascular graft or shunt, a vascular or non-vascular stent, a vascular or non-vascular stent-graft, a patch, such as a patch useful in hemiorraphy or craniosurgery, a material or sheet for dura replacement, and the like.

In another aspect of the present invention, an implantable medical device is provided. The device includes ePTFE having a surface modified by plasma immersion ion implantation; and polysaccharide hydroxyethyl starch groups covalently bonded to the modified surface. The implantable medical device may further include a bioactive agent bonded to the polysaccharide hydroxyethyl starch groups. Useful, but non-limiting, bioactive agents include anti-thrombogenic agents (such as heparin, heparin derivatives, hirudin, acetylsalicylic acid, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; agents which interfere with endogenous vasoactive mechanisms; adhesion factors (such as RGD sequence containing compounds, lysine, poly-L-lysine, antibodies against endothelial cell markers and/or their precursor cells/stem cells, and elastin); and combinations thereof. The implantable medical device may be a graft, including a vascular graft, or a stent-graft, including a vascular stent-graft.

In another aspect of the present invention, an implantable medical device is provided in which the device includes ePTFE having a surface modified by plasma immersion ion implantation; and hydrophilic acrylamide groups covalently bonded to the modified surface. The implantable medical device may further include a bioactive agent bonded, such as one or more of the above-described agents, to the hydrophilic acrylamide groups. The implantable medical device may be a vascular or non-vascular graft or shunt, a vascular or non-vascular stent, a vascular or non-vascular stent-graft, a patch, such as a patch useful in herriorraphy or craniosurgery, a material or sheet for dura replacement, and the like.

In another aspect of the present invention, an implanted, surface modified ePTFE graft includes ePTFE having a node and fibril structure and having a carburized surface formed by plasma immersion ion implantation without destroying the node and fibril structure and having cellular material attached to the fibrils or attached to functional groups covalently bonded to the fibrils and substantially covering and/or filling the nodes. The carburized surface desirably has a depth of about 30 nm to about 500 nm.

In another aspect of the present invention a surface modified ePTFE includes ePTFE having a node and fibril structure and having a carburized surface formed by plasma immersion ion implantation without destroying the node and fibril structure and having seed cells and/or protein material attached to the fibrils and/or attached to spacer groups, preferably hydrophilic acrylamide groups and/or polysaccharide hydroxyethyl starch groups, covalently bonded to the fibril. Useful, but non-limiting, seed cells include epithelial cells (e.g., keratinocytes, hepatocytes), neurons, glial cells, astrocytes, podocytes, mammary epithelial cells, islet cells, endothelial cells (e.g., aortic, capillary and vein endothelial cells), and mesenchymal cells (e.g., adipocytes, dermal fibroblasts, mesothelial cells, osteoblasts), smooth muscle cells, striated muscle cells, ligament fibroblasts, tendon fibroblasts, adult fibroblasts, fibrocytes, chondrocytes, osteocytes, stem cells, genetically modified cells, immunologically masked cells, combinations thereof, and the like. Useful protein material includes fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, kalinin, combinations thereof and the like. Such materials may be useful as a scaffold for seeding cells, i.e., in vitro tissue engineering. The carburized surface desirably has a depth of about 30 nm to about 500 nm.

The following non-limiting examples are intended to further illustrate the present invention.

EXAMPLES

Plasma immersion ion implantation of nitrogen, oxygen and argon ions with different energies and different regimes of treatment was used for the modification of ePTFE sheets, PTFE thin films and low-density polyethylene (LDPE) films. The PTFE and LDPE samples were used as satellite samples for supporting analysis.

Materials and Methods

Materials ePTFE provided by Boston Scientific SCIMED was used for plasma immersion ion implantation treatment, structure analysis and for cell culture experiments. PTFE films of 20 µm and LDPE films of 50 µm were used for plasma immersion ion implantation treatment and structure analysis. The PTFE and LDPE films were cleaned by alcohol before plasma immersion ion implantation. The ePTFE samples were not cleaned before plasma immersion ion implantation, but the surface of the samples was not touched after removing from the packing.

Plasma immersion ion implantation

Most of the modifications were done with the equipment of the Forschungszentrum Rossendorf (FZR), Dresden Germany. The pressure of residual air was $10^{-3}$ Pa, working pressure at discharge was $10^{-1}$ Pa. Nitrogen, oxygen and argon gases were used for plasma discharge. Plasma was generated by radiofrequency generator of 13.56 MHz. Plasma power was regulated in the range of 50-400 W. High voltage pulses were applied to the sample holder at the stable plasma discharge after 0.5-1 minutes after plasma start. The high voltage pulses had 5 µs duration; 20 kV, 10 kV, 1 kV and 0.5 kV values of peak voltage were used. A pulse repetition frequency from 0.2 Hz to 200 Hz was used. The regulation of the pulse frequency was used to control the temperature during the plasma immersion ion implantation treatment. Plasma immersion ion implantation treatment with doses from $10^{13}$ to $10^{16}$ ions/cm$^2$ was carried out for ePTFE, PTFE and LDPE samples.

Additionally, some samples were treated in the Institute of Surface Modification, Leipzig. In this case only nitrogen ions were used with energy of 20 keV. The dose of treatment was $10^{13}$, $10^{14}$, $10^{15}$ and $10^{16}$ cm$^{-2}$.

Figure 4A:
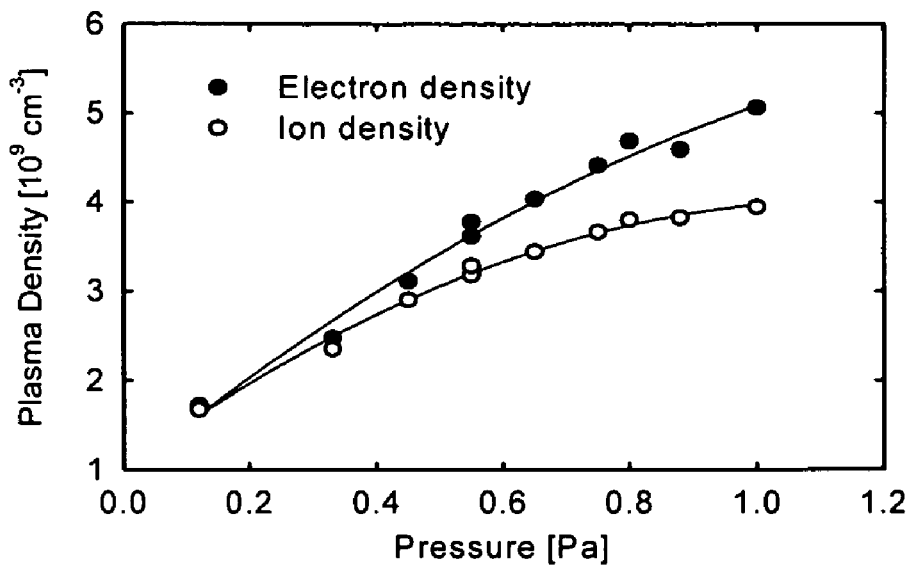
FIGS. 4A and 4B graphically depict plasma densities for nitrogen plasma discharge varying with the pressure of the working gas and the plasma power according to the present invention.
Figure 4B:
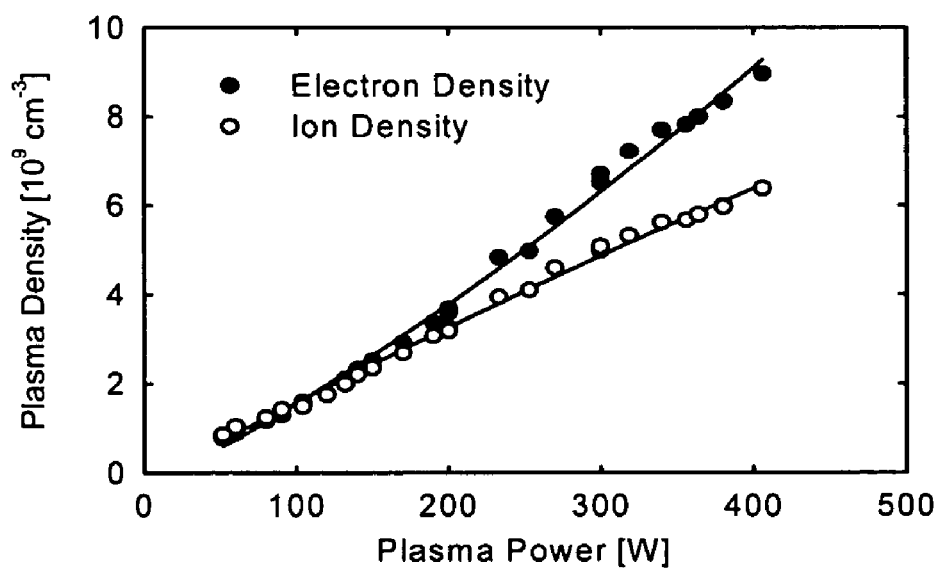

The dose of plasma immersion ion implantation treatment was calculated on direct measurement of plasma density with a Langmuir probe and by comparison of Fourier-Transform-Infrared (FTIR) spectra of the satellite samples of LDPE in comparison with well known previous data. By Langmuir probe the stability of the plasma density was determined and a deviation of dose treatment was estimated as 10% of the average value. For example, the behaviour of plasma density for nitrogen plasma discharge in dependence on pressure of working gas and plasma power are presented in FIGS. 4A and 4B. The plasma density is a function of the chamber pressure and the power used to generate the plasma. The plasma density increases with increases of both of these variables.

The list of the plasma immersion ion implantation regimes used for ePTFE, PTFE and LDPE treatment is presented in Table 1.

TABLE 1

| Chamber Used | Energy [keV] | Dose [ions/cm$^2$] | Working Gas |
| --- | --- | --- | --- |
| FZR | 20 | $10^{13}$, $10^{14}$, $10^{15}$, $10^{16}$ | Nitrogen |
| FZR | 10 | $10^{13}$, $10^{14}$, $10^{15}$, $10^{16}$ | Nitrogen |
| FZR | 1 | $10^{13}$, $10^{14}$, $10^{15}$, $10^{16}$ | Nitrogen |
| FZR | 0.5 | $10^{13}$, $10^{14}$, $10^{15}$, $10^{16}$ | Nitrogen |
| FZR | 20 | $10^{13}$, $10^{14}$, $10^{15}$, $10^{16}$ | Argon |
| FZR | 10 | $10^{13}$, $10^{14}$, $10^{15}$, $10^{16}$ | Argon |
| FZR | 1 | $10^{13}$, $10^{14}$, $10^{15}$, $10^{16}$ | Argon |
| FZR | 0.5 | $10^{13}$, $10^{14}$, $10^{15}$, $10^{16}$ | Argon |
| FZR | 20 | $10^{13}$, $10^{14}$, $10^{15}$, $10^{16}$ | Oxygen |
| FZR | 10 | $10^{13}$, $10^{14}$, $10^{15}$, $10^{16}$ | Oxygen |
| FZR | 1 | $10^{13}$, $10^{14}$, $10^{15}$, $10^{16}$ | Oxygen |
| FZR | 0.5 | $10^{13}$, $10^{14}$, $10^{15}$, $10^{16}$ | Oxygen |
| Leipzig | 20 | $10^{13}$, $10^{14}$, $10^{15}$, $10^{16}$ | Nitrogen |

Chemical Post-Treatment

The modified samples were treated by a 10% solution of acrylamide in water a 10% solution of the modified polysaccharide hydroxyethyl starch in water (HAES sterile 10%, Fresenius AG). The post-treatment was done immediately after plasma immersion ion implantation, as well as after 20 days and after different time of an accelerating ageing procedure. The samples were completely immersed in the solutions for 2 hours at room temperature. After the post-treatment the samples were washed with deionized water and dried on air. The wetting angle measurement of these samples was determined at the following day to exclude any influence of residual water on surface of the polymers.

FTIR ATR Spectra

FTIR ATR spectra were recorded on Nicolet Magna spectrometer with Ge ATR crystal and KRS-6 ATR crystal. Number of scans was 100; spectral resolution was 2 cm$^{-1}$.

Contact Angle Measurement

The measurements of contact angles were done with water and $CH_2I_2$ drops on a Krüss drop shape device using the sessile drop method. The wetting angle was determined by recalculating the drop geometry of video-images and calculating tangents to a baseline.

Accelerating Ageing of Modified ePTFE

Thermal treatment was used for acceleration of ageing processes after plasma immersion ion implantation in modified ePTFE and PTFE samples. The thermobox provided a temperature of 120° C. in dry air. This temperature was selected for ageing test, because of the high stability of PTFE up to 350-400° C., the stability of oxygen-containing products of the surface layer destruction at this temperature but not at higher temperature and a high rate of the free radical quenching at this temperature. Besides that, clinical sterilization by autoclavation also is performed at this temperature.

The ageing processes of polymers are very complex and a precise calculation of the energetic parameters of the ageing processes is impossible. An estimation of the ageing period was done according to Van Hoff's law for temperature dependence of chemical reactions rate. 10° K. increase of temperature represent a duplication of the reaction time. For 100° K. above ambient temperature an accelerated ageing by factor 1000 is expected, 45 min represent 1 month.

Cell Culture

A three-step approach was chosen to select an optimal treatment regime.

Short-term cell performance on single regime treated ePTFE versus untreated ePTFE. This gives some first hints about possibly toxic side products by the ion implantation.

Screening of an array of three ion implantation regimes and two methods of functionalization Further studies with samples of few selected parameter sets.

Step (1)

ePTFE discs were mounted in Minusheets (Minucells and Minutissue, Bad Abbach) and steam sterilized at 120° C. The bovine aortic endothelial cell line GM7373 (Coriell) was used for the experiments. 4×10$^4$ cells in 200 µL medium (MEM- Earle supplemented with 10% FBS, 1×MEM vitamins, 2 mM N-Acetyl L-Alanyl L-Glutamine, 1× Amino acids) were seeded directly on the samples (area 0.58 cm$^2$). They were allowed to adhere for 2 hours at standard cell culture conditions, then medium was filled up to 1 mL per sample.

17 hours after seeding cells of one sample each were fixed in 0.2% paraformaldehyde in PBS and stained with phalloidin-TRITC and DAPI for polymerized actin of the cytoskeleton (red) and cell nuclei (blue). Images were taken by fluorescent microscopy and digitally overlaid.

The other samples with cell culture 17 hours after seeding were placed in 500 μL MEM Earle w/o phenol red, supplemented with 10% FBS, 10% Alamar Blue™. The extinction of the medium was measured after 4.5 hours at λ=570 nm and 600 nm against a blank medium without cells. The value of $(E_{blank,\ 600\ nm} - E_{cells,\ 600\ nm}) + (E_{cells,\ 570\ nm} - E_{blank,\ 570\ nm})$ is a measure of the cell activity. It was calibrated with the activity of defined cell numbers. The number of vital cells on the samples was concluded from their metabolic equivalent.

Toxicity further was tested in a MEM elution test close to DIN EN ISO 10993-5: 1999: An extract of plasma immersion ion implantation treated ePTFE ($10^{16}$ $N_x^+$ cm$^{-2}$), macroscopically 25 cm$^2$ treated surface was steam sterilized at 120° C., 20 min and immersed in 5 mL cell culture medium (MEM Earle with the supplements) in a vial of polypropylene for 46 hours at 37° C. with repeated mixing under sterile conditions. As controls an extract was made of an equivalent amount of untreated ePTFE and medium in an empty vial. Positive controls were medium with $CuCl_2$ in medium (1 mM, 250 μM, 62.5 μM, and 15.5 μM).

1 mL of the extracts was added to 2 cm$^2$ confluent cell layer of GM7373 each. Additionally 1:2, 1:4, and 1:8 dilutions of the extracts with fresh medium were tested. The cells were kept under standard cell culture conditions for three days and inspected for morphological changes daily. At the third day the cell layers were washed once with PBS and the metabolic activity was checked with the chromogenic substrate Alamar Blue™ as described above. The test was performed in duplicate with the extracts and once with the controls.

Step (2)

Samples as in Table 2 were used. Cells were seeded out as described in step (1). An Alamar Blue™ test was performed at day 1,3, and 5. The experiments were performed in duplicate.

TABLE 2

| Label | Energy [keV] | Dose [N cm$^{-2}$] | Functionalization |
| --- | --- | --- | --- |
| Thermanox (1) | — | — | — |
| untreated | — | — | — |
| 1e14 | 20 | $10^{14}$ | — |
| 1e15 | 20 | $10^{15}$ | — |
| 1e16 | 20 | $10^{16}$ | — |
| 1e14 AA | 20 | $10^{14}$ | Acrylamide |
| 1e15 AA | 20 | $10^{15}$ | Acrylamide |
| 1e16 AA | 20 | $10^{16}$ | Acrylamide |
| 1e14 HAES | 20 | $10^{14}$ | HAES sterile 10% |
| 1e15 HAES | 20 | $10^{15}$ | HAES sterile 10% |
| 1e16 HAES | 20 | $10^{16}$ | HAES sterile 10% |

(1) Thermanox ® (Nunc, Wiesbaden) is a polyethylene terephthalate, treated for cell culture applications.

Step (3)

The samples 1e16, 1e16 AA, 1e16 HAES, and 1e14 HAES were selected for further investigation besides the cell culture treated Thermanox® and untreated ePTFE as controls. As used herein, the shorthand of "1e16" and the like may be used interchangeably with $10^{16}$, or the like.

Cells were seeded out as described above, but at various cell densities for the different repeats. An Alamar Blue™ test was performed on day 1 and 3 after seeding. For one set of samples, six hours after seeding cells were fixed with 2% paraformaldehyde and a fluorescent staining was performed as described above.

Results

Color Changes of the Samples

The plasma immersion ion implantation treatment induces a change of color of the samples at high doses. LDPE samples get a metallic shade. PTFE and ePTFE samples become gray. A homogeneous distribution of the color is an indicator of an inhomogeneous dose distribution on the sample surface. In all cases the dose was homogeneously distributed, excluding some edges where samples are attached by metal screws to sample holder. These parts of the samples are excluded from following analysis of the structure and cell experiments.

Molecular Structure of Surface

Plasma immersion ion implantation only modified a thin surface layer of the polymers. Therefore no changes of transmission spectra of the treated samples for all kinds of polymers could be observed.

Figure 5:
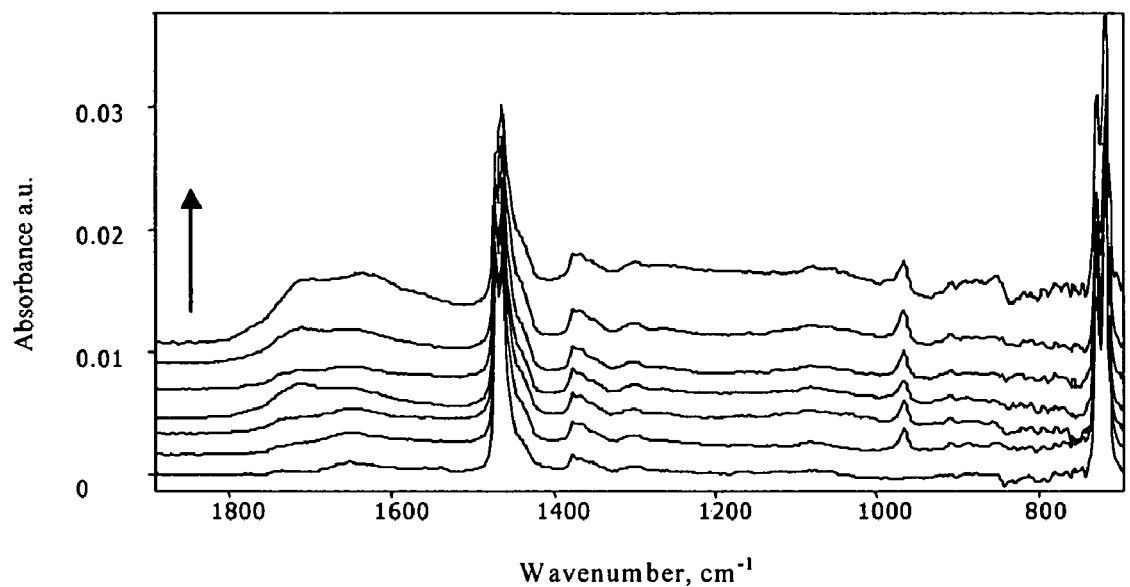
FIG. 5 graphically depicts FTIR spectra of LDPE after plasma immersion ion implantation according to the present invention.

In FTIR spectra of LDPE after plasma immersion ion implantation there are some new spectral lines as depicted in FIG. 5. In FIG. 5, the array shows the dose increase, i.e., initial sample, $10^{13}$, $10^{14}$, $5*10^{14}$, $10^{15}$, $5*10^{15}$, $10^{16}$ ion/cm$^2$, plasma immersion ion implantation of $N^+$ ions at 20 keV energy. The 1750 cm$^{-1}$ line corresponds to carbonyl group vibrations in new oxygen-containing groups, the 1650 cm$^{-1}$ line corresponds to unsaturated carbon-carbon group vibrations in aromatic and unsaturated groups, the field of 1100 cm$^{-1}$ corresponds to oxygen-containing group vibrations like ether groups, the lines at 881, 907 and 968 cm$^{-1}$ correspond to vibrations of unsaturated vinyl, vinylidene and cis-vinylene groups. The appearance of such groups is explained by radiation reactions in surface layer under plasma immersion ion implantation treatment.

Figure 6:
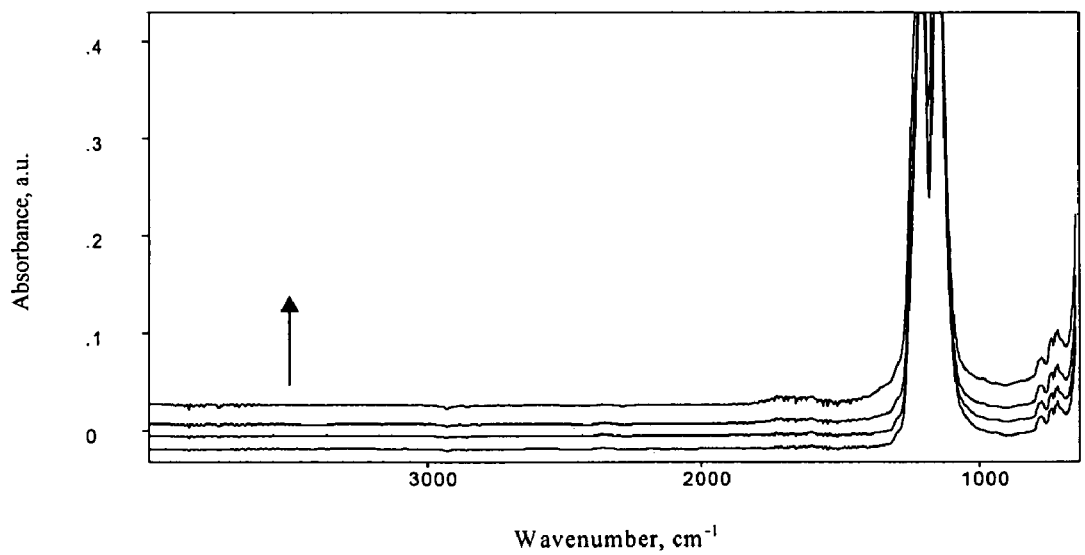
FIG. 6 graphically depicts FTIR ATR spectra of PTFE after plasma immersion ion implantation energy according to the present invention.

FIG. 6 depicts the FTIR ATR spectra of PTFE after plasma immersion ion implantation with N+ at 20 keV. The arrow indicates the plasma immersion ion implantation dose increase: untreated sample, $10^{14}$, $10^{15}$ and $10^{16}$ ions/cm$^2$. As depicted in FIG. 6, the spectra of PTFE the spectral changes were less prominent. The lines at 1750 and 1650 cm$^{-1}$ are observed in the modified samples with low intensity. These lines correspond to appearance of oxygen-containing groups and aromatic condensed structures in PTFE surface layer. The new groups appear due to the destruction processes of the surface layer and reactions of free radicals with oxygen of air after plasma immersion ion implantation treatment. The low intensity of the changes in the FTIR ATR spectra are a consequence of significant differences of the depth resolution of analysis technique and thickness of the modified layer. The thickness of the modified PTFE layer at nitrogen plasma immersion ion implantation at 20 keV is about 100 nm, but the depth of ATR layer analysis for GE crystal equals to 1000-700 nm. Besides that, the sputtering effect of the ions for PTFE is much higher than for LDPE. Therefore plasma modification of PTFE generally does not have a wide application. In the case of plasma immersion ion implantation a carbonization and oxidation of the surface layer of PTFE were observed.

Figure 7:
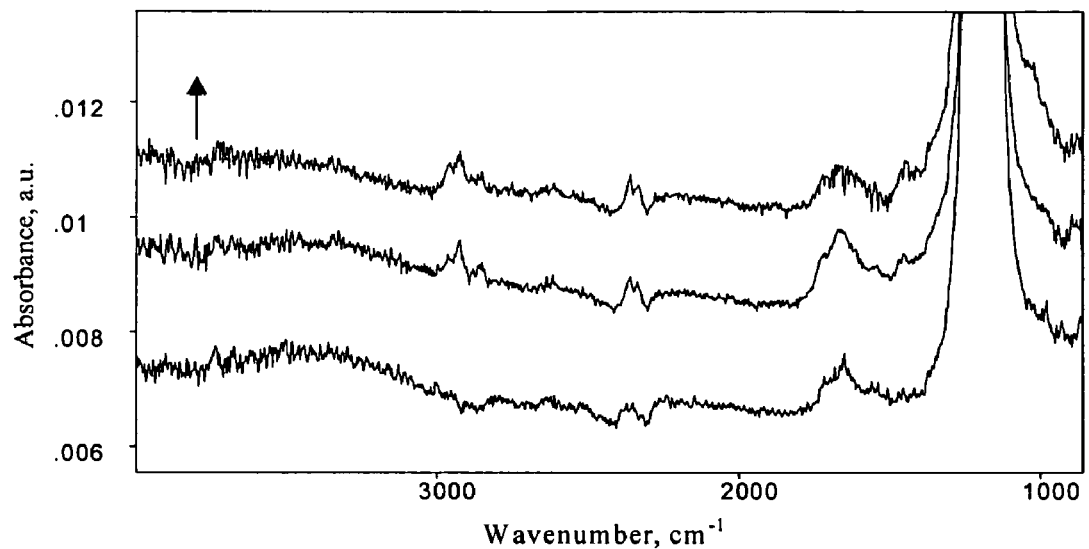
FIG. 7 graphically depicts FTIR ATR spectra of PTFE after plasma immersion ion implantation according to the present invention.

FIG. 7 depicts FTIR ATR spectra of PTFE after plasma immersion ion implantation with N+ at 20 keV and at $10^{16}$ ions/cm$^2$. The samples depicted are as follows: bottom: plasma immersion ion implantation treated sample; middle: post plasma immersion ion implantation treatment by acrylamide; top: post plasma immersion ion implantation treatment by HAES. Due to the ion implantation the PTFE surface showed chemical reactivity. The high activity of free radicals allows a surface modification of PTFE and ePTFE with a wide number of substances. In these experiments the PTFE surface was treated with an acrylamide solution and a HAES solution. In FTIR spectra after acrylamide post-treatment (FIG. 7 middle) there are lines at 2994, 2960, 2924, 2854 $cm^{-1}$ interpreted as stretch vibrations and 1465, 1452 $cm^{-1}$ interpreted as deformation vibrations of C—H bonds in the acrylamide gel on the PTFE surface. These lines do not disappear after washing of PTFE in water. O the untreated reverse side of PTFE these lines could not be observed. After post-treatment of PTFE with HAES (FIG. 7 top) the spectra contain the lines at 2956, 2925, 2855, 1451 $cm^{-1}$ interpreted as C—H stretch and deformational vibrations of the crosslinked HAES layer. The line at 1028 $cm^{-1}$ in wind of the strong PTFE line is interpreted as C—O vibrations of HAES layer. This layer is observed only on the treated side of PTFE and is stable after washing of the ePTFE.

Figure 8:
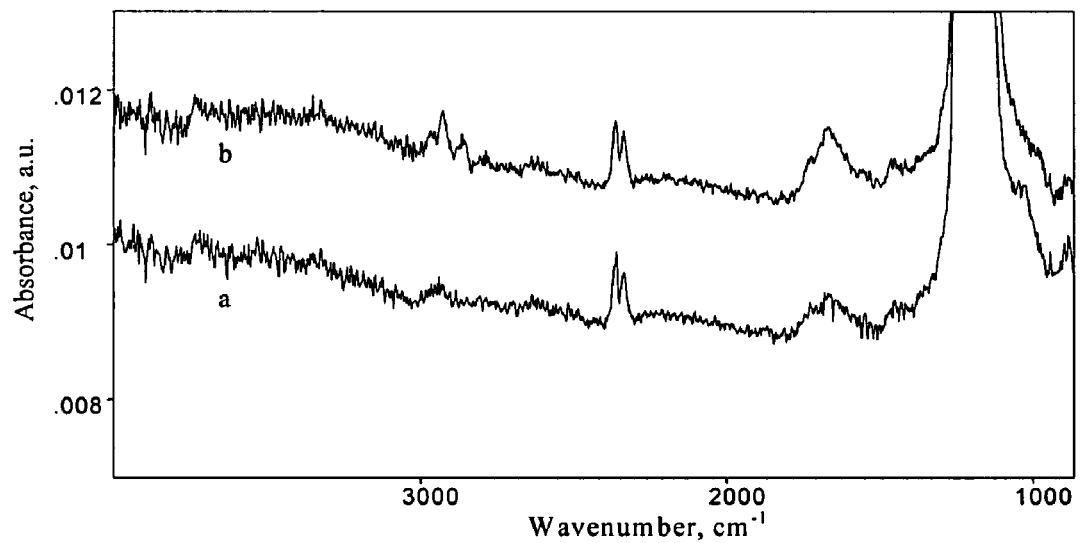
FIG. 8 graphically depicts FTIR ATR spectral of ePTFE samples after plasma immersion ion implantation treatment and post-treatment by acrylamide and polysaccharide hydroxyethyl starch according to the present invention.

As depicted in FIG. 8, the same spectral changes were observed for ePTFE samples after plasma immersion ion implantation treatment and post-treatment by acrylamide and HAES. FIG. 8 depicts the FTIR ATR spectra of ePTFE, 20 keV, N+, $10^{16}$ ions/$cm^2$: a—HAES post-treatment, b—acrylamide post-treatment.

Figure 9:
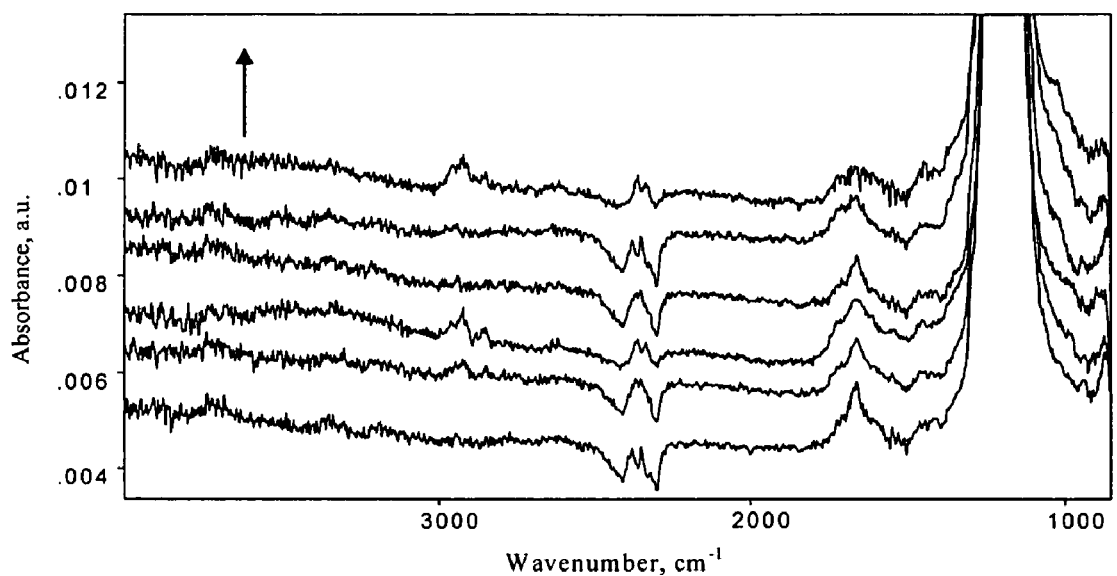
FIG. 9 graphically depicts FTIR ATR spectra of PTFE after plasma immersion ion implantation treatment and post-treatment by acrylamide and by polysaccharide hydroxyethyl starch according to the present invention.

FIG. 9 depicts the FTIR ATR spectra of PTFE, plasma immersion ion implantation treatment, 20 keV, N+, by arrow: $10^{14}$, $10^{15}$, $10^{16}$ ions/$cm^2$ and post-treatment by acrylamide, $10^{14}$, $10^{15}$, $10^{16}$ ions/$cm^2$ and post-treatment by HAES. FIG. 9 shows that there was a dose dependence of the treatment dose and the amount of crosslinked acrylamide and HAES.

Figure 10:
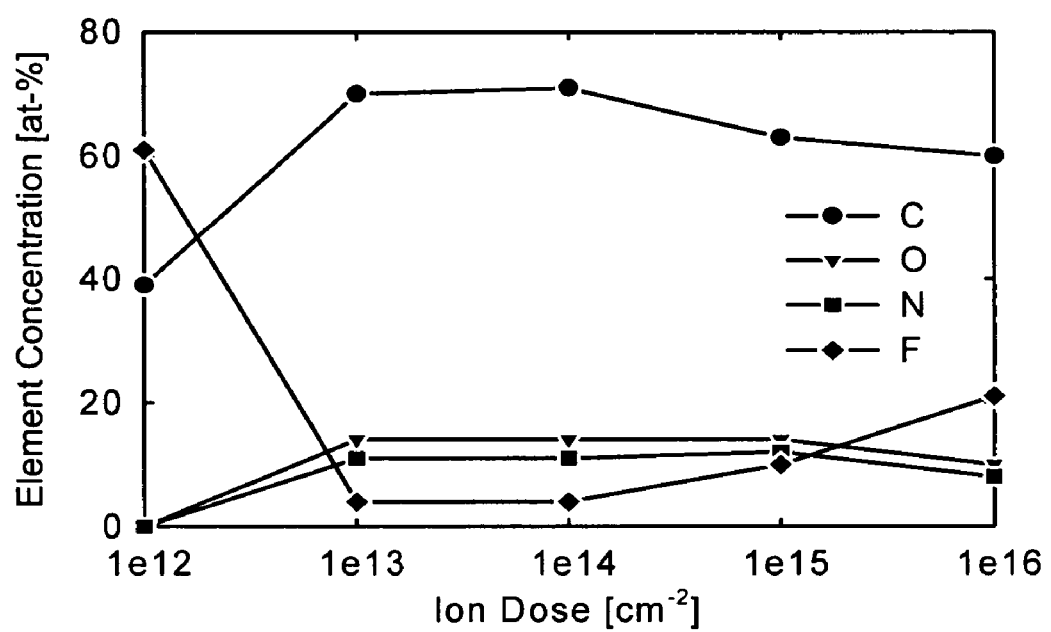
FIG. 10 graphically depicts element concentration in PTFE surface in dependence on plasma immersion ion implantation dose treatment according to the present invention.

FIG. 10 depicts element concentration in PTFE surface in dependence on plasma immersion ion implantation dose treatment ($N^+$, 20 keV). Curves were generated by XPS data. Strong chemical changes of PTFE could be observed by XPS, which were used for element contamination analysis of the surface layer of PTFE after plasma immersion ion implantation. In modified PTFE the contamination of fluorine atoms was significantly lower then in initial. The relative concentration of carbon atoms increased. The appearance of nitrogen and oxygen atoms was observed. However, there was no strong dependence of the atomic concentrations of elements on dose of plasma immersion ion implantation treatment. Even at low dose, the surface layer of PTFE contained a significant amount of oxygen and nitrogen atoms. At high dose, the effect of etching became significant and the concentration of fluorine atoms started to increase again, parallel with a decrease of oxygen and nitrogen. This indicates that the etching effect becomes significant at high dose treatment.

Figure 11:
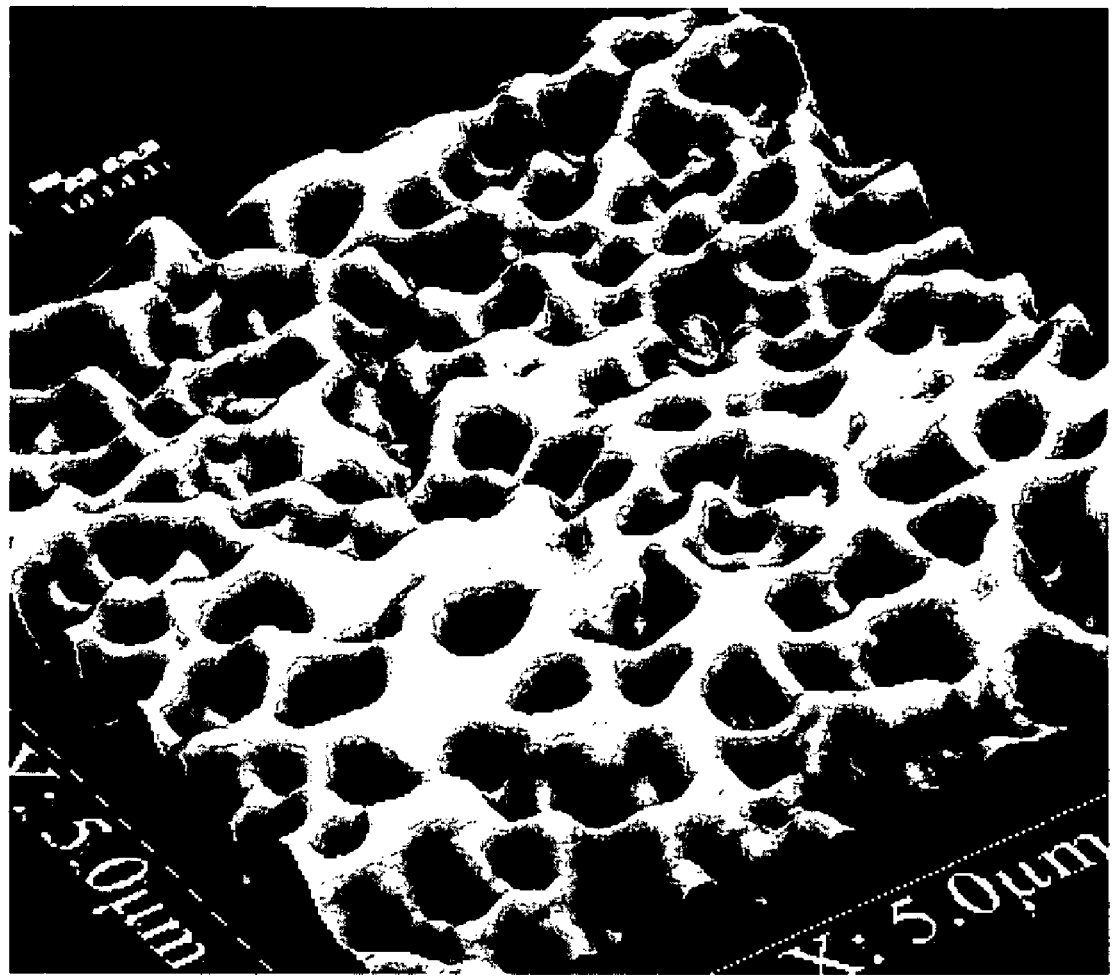
FIG. 11 depicts increased roughness of the PTFE surface modified by plasma immersion ion implantation according to the present invention.

The etching process also could be demonstrated morphologically on the PTFE surface. As depicted in FIG. 11, atomic force microscopy (AFM) shows an increased roughness of the PTFE surface modified by plasma immersion ion implantation with $N^+$ at 20 keV. Although etched, the node and fibril structure of the modified ePTFE was not destroyed or substantially altered.

Parallel with the molecular structure the wettability of the surface changed. For example, water drops were placed on ePTFE, PTFE and LDPE surfaces. There was clear difference of the wettability on treated surfaces. The water drop on initial ePTFE could not be placed by the steel cannula. The drop did not stay on the polymer surface but attached to the needle. For measurements the drops fell down to the surface and were measured then. For the treated ePTFE surface the drops were put from needle at usual procedure.

The contact angles of the water drops changed dramatically after plasma immersion ion implantation treatment. Low dose treatment induced higher hydrophilicty. At high doses the effect of etching and carbonization caused a decrease of wettability. This was observed both for PTFE and LDPE samples. The wetting measurement of ePTFE directly by the wetting angle technique is inadequate, because of the abnormal form of the drop. But the chemical structure of ePTFE and PTFE is quite similar and allows the transfer of the wetting measurement results of PTFE to ePTFE samples.

Figure 12:
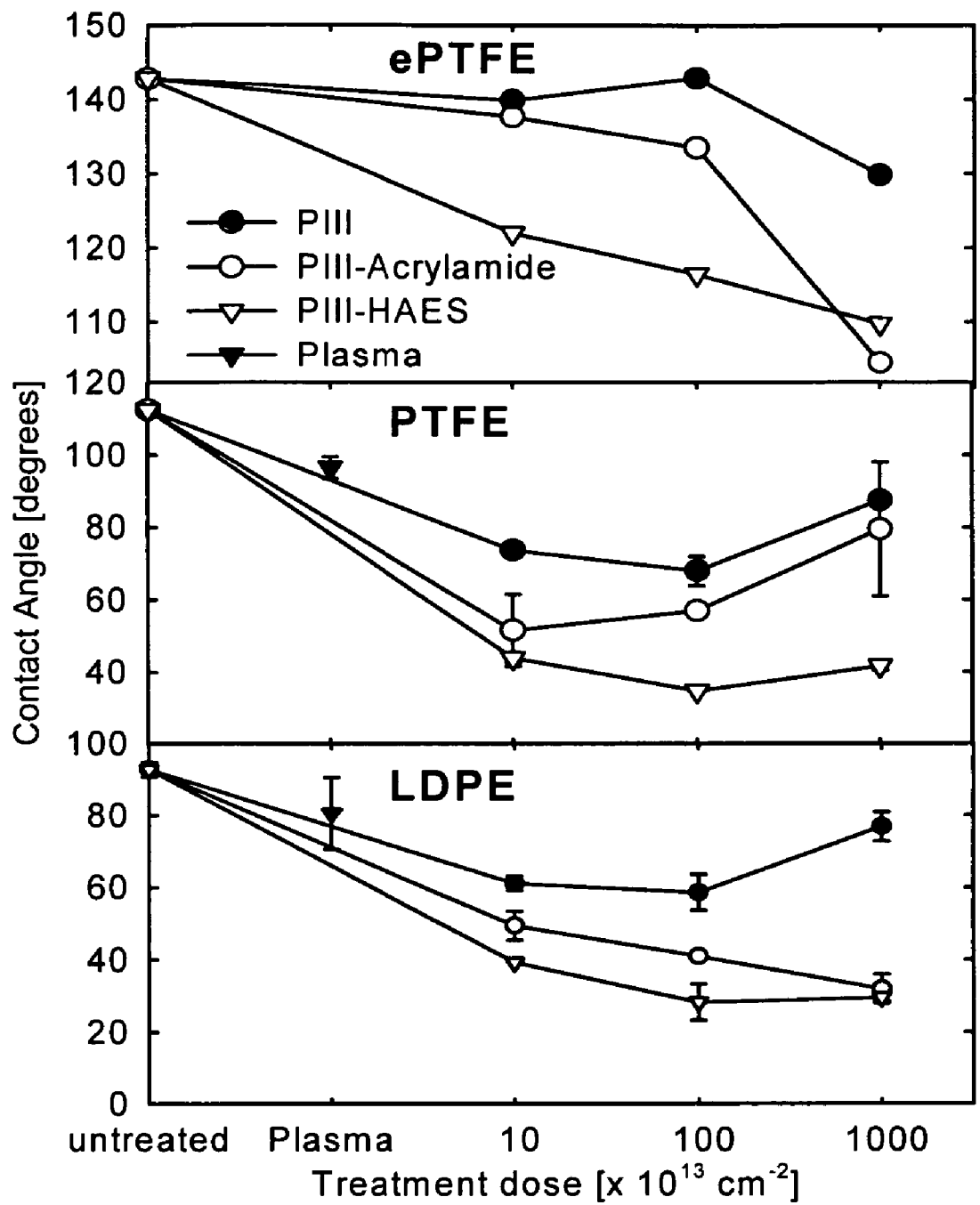
FIG. 12 graphically depicts contact angles of water on ePTFE, PTFE, and LDPE after plasma immersion ion implantation treatment post-treatment according to the present invention.

FIG. 12 depicts contact angles of water on ePTFE (top), PTFE (middle), and LDPE (bottom) with plasma immersion ion implantation treatment with $N^+$ at 20 keV and post-treatment as indicated. At post-treatment by acrylamide and HAES the wetting angles of PTFE and LDPE decreased to very low values of 20-30 degrees. This wettability is similar as for metal surfaces. The treatment dose of $10^{14}$ and $10^{15}$ ions/$cm^2$ is enough for a good wettability. At high dose the effect of etching for PTFE surface also was is observed for post-treated surfaces.

Influence of Silicon Deposition

In some experiments, unintendedly, some silicon deposition on polymer surface was observed. The reason was in previous experiments in the chamber with spattering of a silicon target and deposition of silicon on substrates, which had caused some remaining contamination. The deposition effect was observed by FTIR ATR spectra of LDPE. The strong intensity lines at 1090 and 1167 $cm^{-1}$ appeared in the spectra after plasma immersion ion implantation. These lines are interpreted as vibrations of Si, $SiO_2$ and Si—C structures. In the field of 3400 $cm^{-1}$ a wide line of Si—OH vibrations was observed. The intensity of these lines did not depend on the dose of plasma immersion ion implantation and energy of ions, but the amount of Si-containing structures depended on time in plasma chamber. So, after plasma immersion ion implantation and silicon deposition the surface of polymer contained a $Si_xC_yO_z$ layer as combination of different structures.

Decreasing of plasma immersion ion implantation treatment time by increasing of pulse repetition frequency did not could reduce the formation of the $Si_xC_yO_z$ layer, but did not exclude it. The effect of Si-deposition was observed for different regimes of plasma immersion ion implantation, different types of ions, energies and pulse frequencies.

However, the FTIR ATR spectra of ePTFE did not show any changes in comparison with untreated sample. The spectra had a low intensity of polytetrafluoro-macromolecule vibrations in comparison with PTFE film. The intensity of the macromolecule lines was more than 10 times lower than at samples without silicon deposition. The reason is the pore structure of ePTFE and the insufficient optical contact between the ATR crystal and ePTFE surface for contrast spectra. In comparison with ePTFE after pure plasma immersion ion implantation, at silicon deposition, there were no spectral changes corresponding to the carbonization of the surface layer under ion bombardment. The color of the ePTFE changed less than at pure plasma immersion ion implantation. This indicates a protective effect of the deposited layer on the ePTFE surface.

The contact angle measurements showed a strong influence of silicon deposition. The wetting angle depends on amount of Si—O—H groups and wettability can be very high. On the other side, at high doses of plasma immersion ion implantation the effect of interpenetration of Si atoms into deep layers leads to increase of the contact angles.

Ageing of Plasma Immersion Ion Implantation Treated Surfaces

The ageing test was done for an analysis of stability of the modified surfaces after plasma immersion ion implantation.

The stability of the surface was estimated by contact angle measurement of a water drop after thermal ageing and after ageing and treatment by HAES. In the second case, not only wettability was tested, but the ability of the treated surface to preserve the chemical activity during ageing.

Figure 13A:
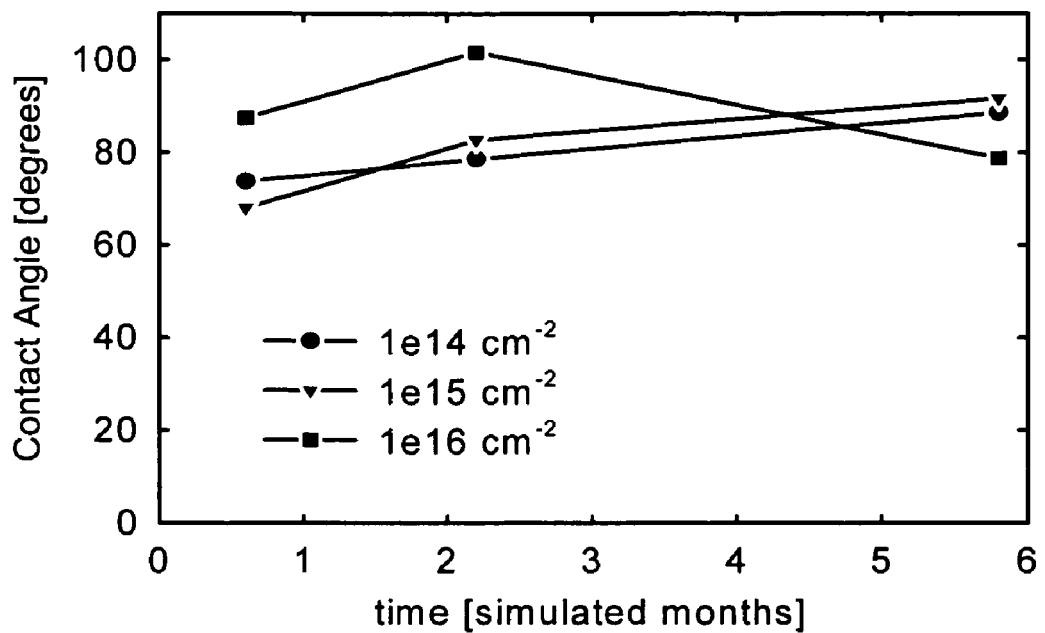
FIGS. 13A and 13B graphically depict ageing kinetics of ePTFE and PTFE according to the present invention.

In the experiment, the samples of PTFE and ePTFE were treated by plasma immersion ion implantation at three different does, i.e., $10^{14}$ ions/cm$^2$, $10^{15}$ ions/cm$^2$ and $10^{16}$ ions/cm$^2$, as shown, and then treated by elevated temperature, which was used as model of the ageing process (time-temperature superposition). After thermal treatment the contact angles of PTFE remained mainly unchanged (FIG. 13A). The ageing kinetics shows that the hydrophilicty of treated PTFE can be preserved at least for several months.

Figure 13B:
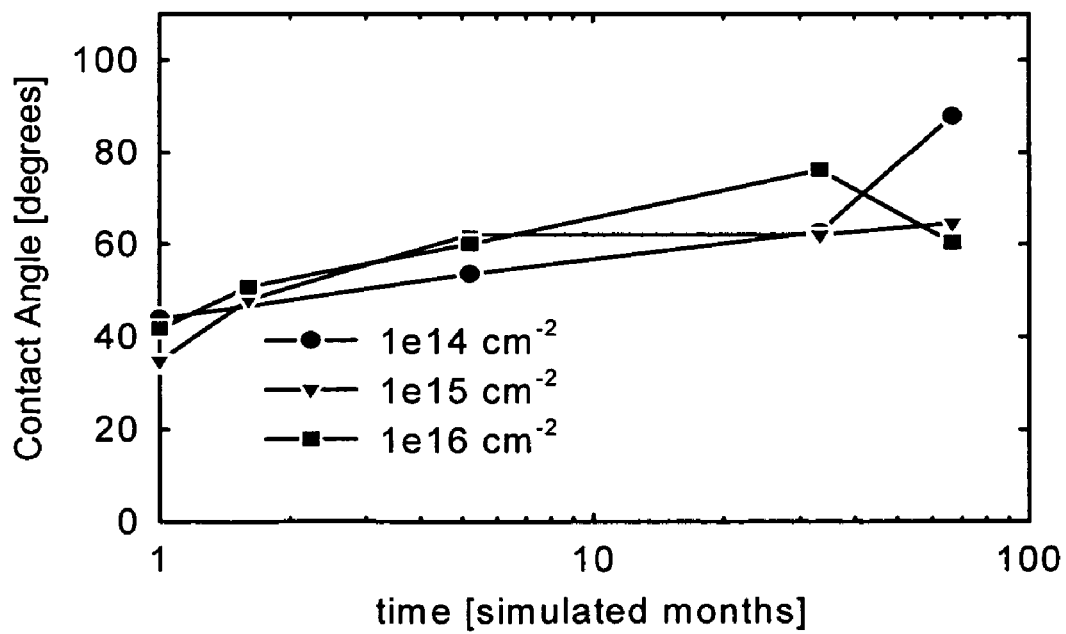

At the second stage of experiments the plasma immersion ion implantation modified samples after thermal treatment were treated with HAES and the wetting angles were measured. The contact angles increased with time of ageing (FIG. 13B). This indicates that the aged PTFE surface had less activity and less amount of HAES molecules reacted with the PTFE modified layer. The chemical activity of modified PTFE decreases with time. The chemical activity of the modified PTFE surface cannot be kept constant over several months after plasma immersion ion implantation modification.

The kinetics of the modified ePTFE samples had a more complex character. The wettability of an untreated sample decreased with time of thermal ageing. Increase of wetting angle cannot be explained by oxidation or destruction processes of the ePTFE macromolecules. Mainly the etching effect should lead to the increased hydrophobicity as releasing of waste products from the surface layer of PTFE and appearance of an initial non-defected ePTFE surface layer.

Figure 14A:
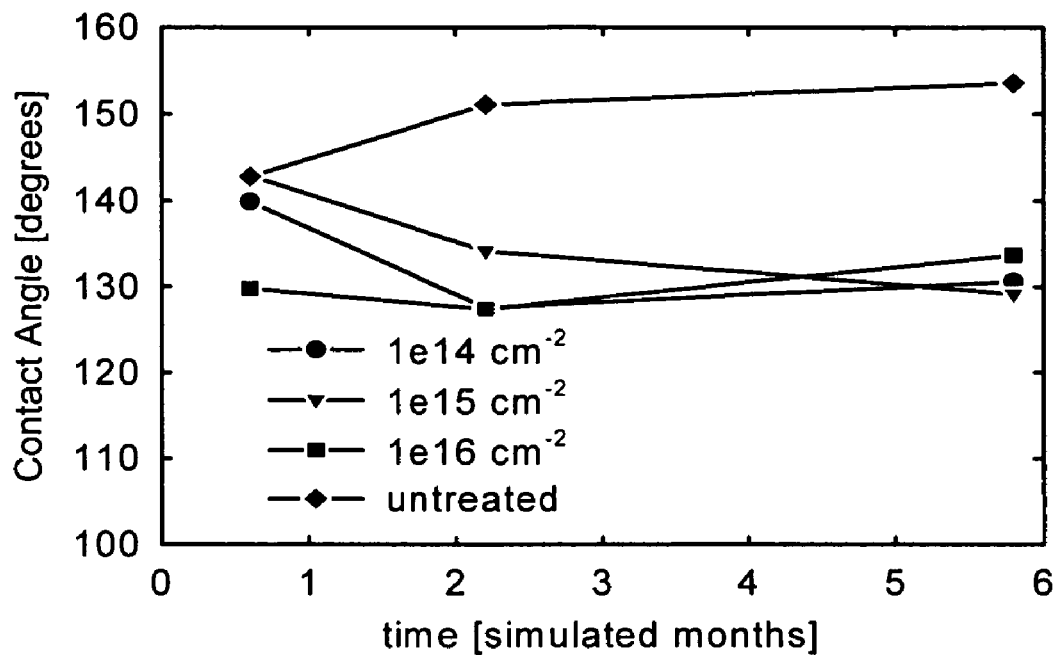
FIGS. 14A and 14B graphically depict accelerated ageing kinetics of ePTFE and PTFE according to the present invention according to the present invention.
Figure 14B:
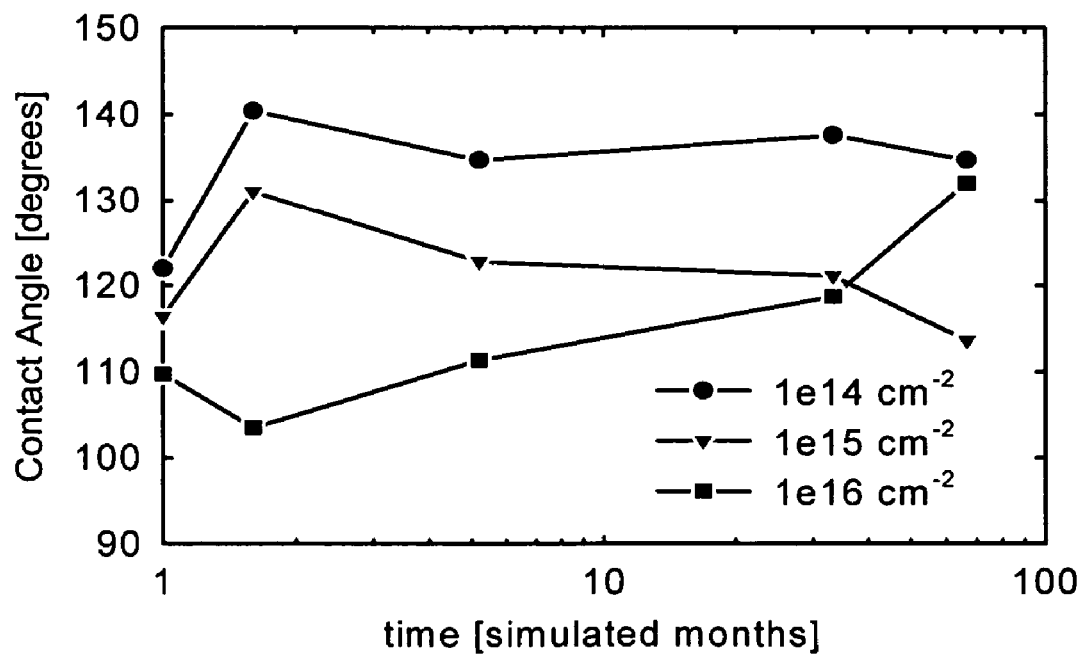
Figure 15A:
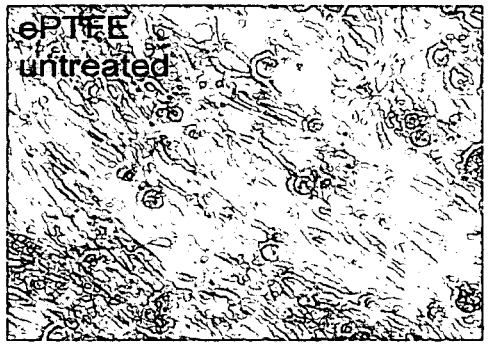
FIG. 15A through 15D depict morphology of GM7373 cells after exposure to extracts of ePTFE according to the present invention.
Figure 15B:
Figure 15C:
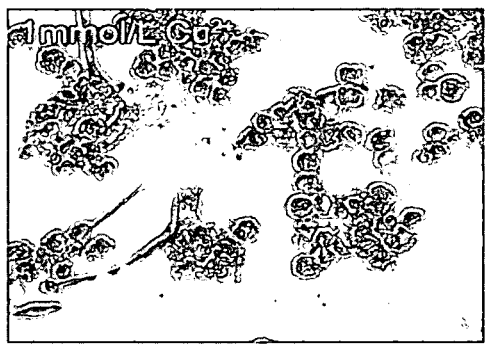
Figure 15D:
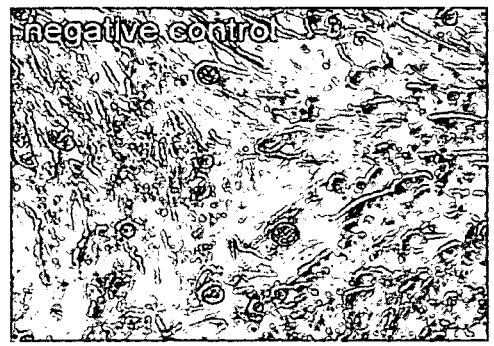

In the case of modified ePTFE samples, a decrease of wetting angles with time of the ageing shows the structure transformation of the surface layer. The ageing of the ePTFE chemical activity shows more complex character. Taken into account the complex dependence of wettability of rough surfaces, the ageing kinetics by wetting angles have only preliminary character. These effects are depicted in FIGS. 14A and 14B, which show ePTFE contact angle as function of time in accelerated ageing. FIG. 14A is for ePTFE plasma immersion ion implantation with N$^+$, implanted at the indicated doses of $10^{14}$ ions/cm$^2$, $10^{15}$ ions/cm$^2$ and $10^{16}$ ions/cm$^2$. FIG. 14B is for ePTFE plasma immersion ion implantation with N$^+$, implanted at the indicated doses of $10^{14}$ ions/cm$^2$, $10^{15}$ ions/cm$^2$ and $10^{16}$ ions/cm$^2$ and HAES post-treated.

Cell Culture

Step (1)

The purpose of this step mainly was to check, whether plasma immersion ion implantation treatment of ePTFE causes the release of toxic by-products. For this no dose optimization or functionalization was applied. Cells used were GM7373 bovine aortic endothelial cells.

The metabolic activity of the cells on the samples was equivalent to 23% of total seeded cells on untreated ePTFE and 38% of total seeded cells on plasma immersion ion implantation treated ePTFE.

On the untreated ePTFE the initial polymer cells were small and round. Mainly they were between the ePTFE fibrils without direct contact thereto, only few adhered locally to the substrate. On treated ePTFE cells had an elongated body, which were aligned to the ePTFE fibrils. A cytoskeleton of polymerized f-actin was built up only on the plasma immersion ion implantation treated ePTFE, whereas on the untreated one the actin in the cells formed unorganized aggregates.

The MEM elution test after three days did not show obvious morphologic differences of the cells with extracts from plasma immersion ion implantation treated (N$^+$ at $10^{16}$ ions/cm$^2$) or untreated ePTFE or the negative control. The 1 mM Cu$^{2+}$, however caused severe cell damage. However, the inspection revealed a lot of fibrillar particles in the extract of irradiated ePTFE, what seemed to exceed the number of particles in the extract of initial ePTFE. The morphology of GM7373 cells after three days exposure to extracts of ePTFE, Cu$^{2+}$ as positive control and a negative control are depicted in FIGS. 15A through 15D.

Figure 16:
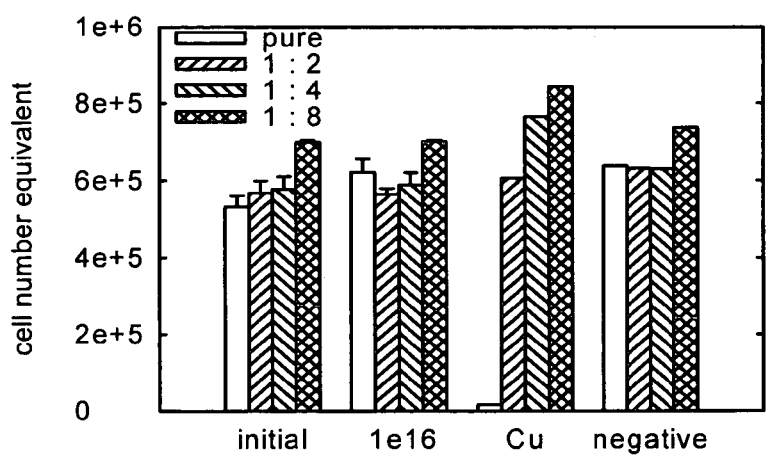
FIG. 16 graphically depicts cell count or activity of GM7373 cells after exposure to with extracts of untreated and treated ePTFE according to the present invention.

The exposure to medium, which was used in forming an extract generally, resulted in a slightly lower cell activity after three days than fresh medium. This behavior was dose dependent and independent, whether initial or plasma immersion ion implantation treated ePTFE was used. The positive control copper was toxic only in the highest concentration, whereas low concentrations even stimulated the metabolism as depicted in FIG. 16 in which cell count/activity of GM7373 cells after three days exposure to with extracts of untreated ePTFE and nitrogen irradiated ($10^{16}$ cm$^{-2}$) ePTFE versus controls. Various dilutions with fresh medium were applied as indicated, Cu$^{2+}$, respectively, was used in the concentrations 1000, 250, 63, and 15.6 μmol/L.

Step (2)

The purpose of this step was a brief screening of different implantation regimes and regimes of functionalization.

Figure 17:
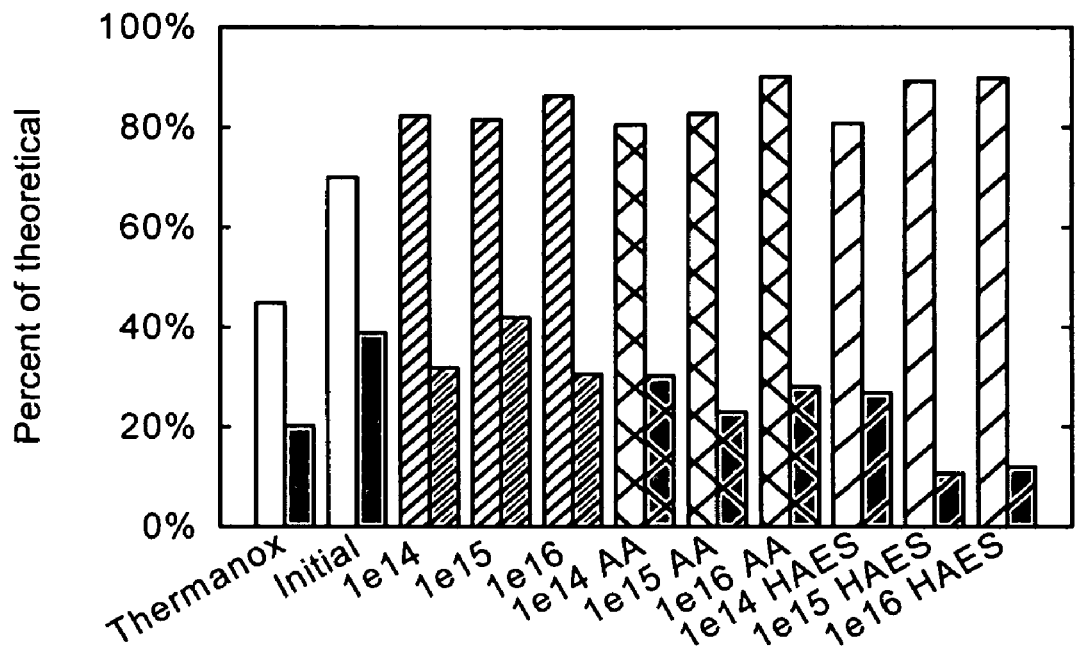
FIG. 17 graphically depicts cell count or activity of GM7373 cells after exposure to with extracts of untreated and treated ePTFE and control material according to the present invention.

Because of the generally low cell activity of cells on the substrates in the step (1) experiments, the cell culture plastic Thermanox was included here as a reference. On all ePTFE substrates the cell activity at day 1 was higher than on Thermanox. The cell activity was further clearly higher on the ion implanted ePTFE samples. Independent of the functionalization with acrylamide or with HAES, there seemed to be a dose dependence of cell performance from the implantation dose, as indicated in FIG. 17. FIG. 17 depicts cell activity of GM7373 cells after 1 (white bars) and 3 days (gray bars) on the substrates as indicated, i.e., Thermanox, initial or untreated PTFE, PTFE treated at ion concentrations of $10^{14}$ ions/cm$^2$, $10^{15}$ ions/cm$^2$, $10^{16}$ ions/cm$^2$, $10^{14}$ and $10^{15}$ ions/cm$^2$ with acrylamide post treatment, and $10^{14}$, $10^{15}$ and $10^{16}$ ions/cm$^2$ with HAES post treatment. The patterns indicate the corresponding groups: the value of the third day was obtained by extended culture of the cells after the first Alamar Blue™ test; the 100% reference is the same number of cells seeded on the bottom of a cell culture well.

After the Alamar Blue™ test at day 1 the cells were further cultured and the metabolic activity was determined again at day 3. For all types of sample there the cell performance was dramatically decreased. At day 5 almost no activity could be measured any more; fluorescent stain for the cell mitochondrial potential with JC-1 did not show any sign of vitality. Stain for cell nuclei and f-actin also only showed remainings of dead cells at day 5. It is more probable that this cell death is an effect of the specific cell culture conditions with the Minusheet supports and the repeated Alamar Blue™ test; both factors caused an unusual high oxygen partial pressure to the cells, which might induce oxidative stress. However, long-term investigations without intermitted metabolic tests were not performed.

Step (3)

According to the findings in step (2) the highest dose treatment had the best effect on cell adherence, therefore $10^{16}$ cm$^{-2}$ implanted samples with different functionalization were compared in more detail in this step.

In the same regime the Alamar Blue™ test was performed at day 1 and 3 after seeding the cells. The drop in cell activity at day 3 was compensated by normalizing the values to Thermanox as 100%.

Figure 18:
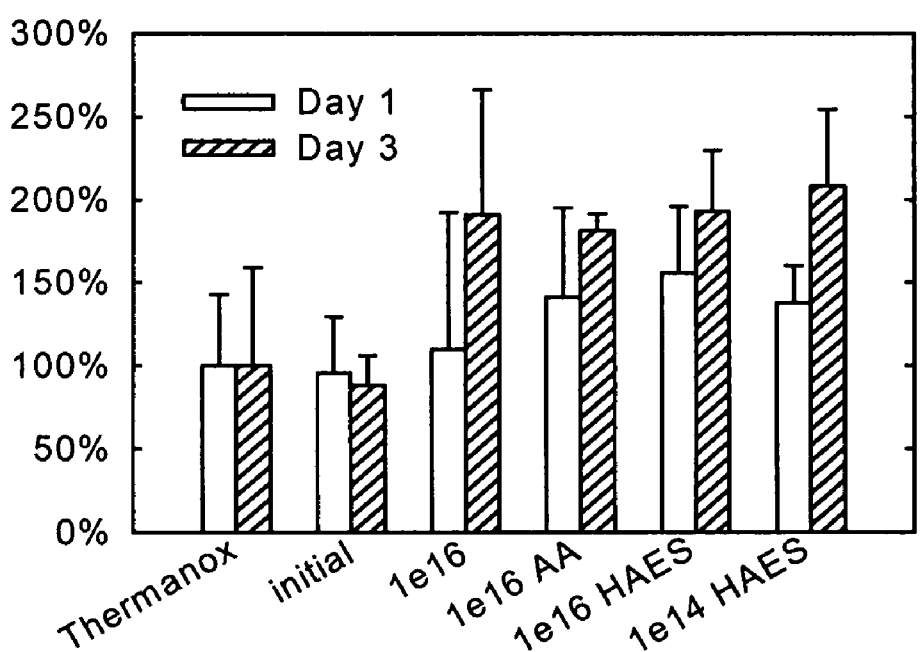
FIG. 18 graphically depicts cell count or activity of repeated experiments on a subset of samples from FIG. 17, normalized to the control material according to the present invention.

Confirming the previous results, ion treatment improved the cell performance. This was even more pronounced at day 3 than at day 1. Functionalization either with acrylamide or with HAES had the main effect for initial adherence of the cells, but les for the longer performance. Also the dose effect was more pronounced early after seeding than at a later stage, as depicted in FIG. 18, which shows cell activity normalized to Thermanox® as 100%.

There was good cell spreading and the characteristic formation of a cobblestone-like monolayer of the cells on Thermanox. The endothelial cells also adhere and spread on the plasma immersion ion implantation treated and functionalized ePTFE, however, there the distinct arrangement of the cells was not present on the multifilament surface. Spreading of the cells also was seen on plasma immersion ion implantation treated ePTFE without functionalization. On untreated ePTFE, cells mainly aggregated and did not adhere to the substrate.

CONCLUSIONS

Plasma immersion ion implantation was used for modification of ePTFE, PTFE and LDPE surfaces. The plasma immersion ion implantation treatment was done at different regimes, different gases, on two different plasma immersion ion implantation chambers. The modification of polymer structures was observed by FTIR, XPS, wetting angle measurements. The testing showed the changes of molecular structure of surface layer, wettability changes, chemical activity changes and element contamination changes.

The effect of accelerated ageing of modified surfaces after plasma immersion ion implantation was observed. The wetting and chemical activity of PTFE and ePTFE surfaces were observed at ageing tests.

It was shown that such treated ePTFE does not release toxic degradation products to the medium, which would inhibit the growth or metabolism of endothelial cells. In a static system the bovine aortic endothelial cell line GM7373 clearly adhered better on the ion treated ePTFE. There also was a higher metabolic activity of the cells on such treated samples, what can express both a higher activity of the individual cells or higher absolute number of vital cells. The effect was slightly dose dependent. However, for high dose treatment the ePTFE fibrils also tended to become more brittle. This was seen at the higher particle release in the extracts. Highly biostable particles of the size found here, in vivo tend to induce foreign body granulomas. Optimization of the treatment parameters and extensive washing processes have to be performed in order to avoid this problem.

Treatment with higher energetic ions, ion implantation induced carburization of the surface, which prevented surface remodelling. Ion implantation into polymers also lead to the formation of dangling bondings and free radicals in the polymer surface. Even though no effect was seen here, these free radicals are potentially toxic for adherent cells. Therefore these bondings were saturated with the highly hydrophilic acrylamide. The substance by this process covalently bonds to the polymer surface and free monomers of the toxic substance were washed out. In the experiments described above a better performance of acrylamide treated ion implanted ePTFE was shown. Alternatively to acrylamide, the modified polysaccharide hydroxyethyl starch or HAES was also used to saturate the free radicals on the polymer surface. HAES is in clinical application as plasma expander for the treatment of hypovolaemia and shock. Due to the substitution it is better soluble in water than ordinary starch and more resistant against degradation. In solution it tends to inhibit haemostatic processes by interaction with clotting factors and blood platelets. Endothelial cells also internalize the free form by pinocytosis and eliminate only about 50% of it. The expression of activation markers is not modulated by this, but HAES directly inhibits the interaction with polymorphonuclear neutrophils.

In this study, HAES may be also seen more as a model substance, which can be used to functionalize the surface. It can be either substituted with glucosaminogycans like heparin, or direct modification of the hydroxyethyl group e.g. with the before mentioned elastin or peptides would be possible. To our knowledge, this would be a new approach to functionalize the ePTFE surface for a specific and strong adherence of endothelial cells.

The invention being thus described, it will now be evident to those skilled in the art that the same may be varied in many ways. Such variations are not to be regarded as a departure from the spirit and scope of the invention and all such modifications are intended to be included within the scope of the following claims.

What is claimed is:

1. A method for modifying an ePTFE surface, comprising:
providing an ePTFE material in a chamber suitable for plasma treatment;
providing a continuous low energy plasma discharge onto the ePTFE material;
applying high voltage pulses of short duration to form a high energy ion flux from the plasma discharge to generate ions which form free radials on the surface of the ePTEE material;
dosing the ions onto the ePTFE material at about $10^{13}$ to about $10^{16}$ ions per cm$^2$ of the surface of the ePTFE material; and
carburizing the ePTFE material to a depth of about 30 nm to about 500 nm to define a modified ePTFE surface without destroying the node and fibril structure of the ePTFE material below the modified ePTFE surface.

2. The method of claim 1, wherein the step of providing the continuous low energy plasma discharge onto the ePTFE material, comprises:
generating the plasma discharge at a radiofrequency of about 13.56 MHz or about 2.45 GHz.

3. The method of claim 1, wherein the step of providing the continuous low energy plasma discharge onto the ePTFE material, comprises:
providing a source of gas from which the plasma is generated, wherein the gas is selected from the group consisting of nitrogen, oxygen, argon and combinations thereof.

4. The method of claim 1, wherein the step of applying high voltage pulses for a short period of time to form an ion flux from the plasma discharge, comprises:
applying voltages from −0.5 kV to −40 kV.

5. The method of claim 1, wherein the step of applying high voltage pulses for a short period of time to form an ion flux from the plasma discharge, comprises:
applying voltages from −0.5 kV to −20 kV.

6. The method of claim 1, wherein the step of applying high voltage pulses for a short period of time to form an ion flux from the plasma discharge, comprises:
applying voltages at a frequency from 0.2 Hz to 200 Hz.

7. The method of claim 1, wherein voltages are applied for a duration of about 1 to about 10 microseconds.

8. The method of claim 1, wherein voltages are applied for a duration of about 5 microseconds.

9. The method of claim 1, wherein power to generate the plasma discharge is from about 50 watts to about 500 watts.

10. The method of claim 1, further comprising:
providing the chamber with an operating pressure from about 0.1 Pa to about 1.0 Pa.

11. The method of claim 1, further comprising:
oxidizing at least a portion of the free radials.

12. The method of claim 1, further comprising:
functionalizing the free radical sites with a spacer molecule or material, wherein the spacer molecule or material is covalently bonded to the modified ePTFE surface.

13. The method of claim 1, further comprising:
functionalizing the free radical sites with hydrophilic acrylamide groups.

14. The method of claim 13, further comprising:
covalently bonding the hydrophilic acrylamide groups to the modified ePTFE surface.

15. The method of claim 14, further comprising:
covalently bonding a bioactive agent bonded to the hydrophilic acrylamide groups that are covalently bonded to the modified ePTFE surface.

16. The method of claim 1, further comprising:
functionalizing the free radical sites with polysaccharide hydroxyethyl starch groups.

17. The method of claim 16, further comprising:
covalently bonding the polysaccharide hydroxyethyl starch groups to the modified ePTFE surface.

18. The method of claim 17, further comprising:
covalently bonding a bioactive agent bonded to the polysaccharide hydroxyethyl starch groups that are covalently bonded to the modified ePTFE surface.

19. The method of claim 1, further comprising:
covalently bonding a bioactive agent bonded to the modified ePTFE surface.

20. The method of claim 19, wherein the bioactive agent is selected from the group consisting of anti-thrombogenic agents, anti-proliferative agents, anti-inflammatory agents, antineoplastic/antiproliferative/anti-mitotic agents, anesthetic agents, anti-coagulants, vascular cell growth promotors, vascular cell growth inhibitors, cholesterol-lowering agents, vasodilating agents, agents which interfere with endogenous vasoactive mechanisms, cell adhesion factors; and combinations thereof.

21. The method of claim 1, wherein the ePTFE material is an implantable medical device.

22. The method of claim 21, wherein the implantable medical device is a vascular graft.

23. The method of claim 21, wherein the implantable medical device is a vascular stent-graft.

24. A method for modifying an ePTFE surface, comprising:
providing an ePTFE material in a chamber suitable for plasma treatment;
generating a continuous low energy plasma discharge at a radiofrequency of about 13.56 MHz or about 2.45 GHz;
applying high voltage pulses from −0.5 kV to −40 kV at a frequency from 0.2 Hz to 200 Hz for short duration of about 1 to about 10 microseconds to form a high energy ion flux from the plasma discharge to generate ions which form free radials on the surface of the ePTFE material; and
dosing the ions onto the ePTFE material at about $10^{13}$ to about $10^{16}$ ions per $cm^2$ of the surface of the ePTFE material to form free radials thereby defining a modified ePTFE surface without changing the molecular and/or physical structure of the ePTFE material below the modified ePTFE surface;
wherein the ePTFE material has a node and fibril structure and wherein the step of applying the high voltage pulses modifies the surface of the ePTFE without destroying the node and fibril structure.

25. The method of claim 24, wherein the ePTEE material has a node and fibril structure and wherein the step of applying the high voltage pulses etches and/or carburizes the surface of the ePTFE without destroying the node and fibril structure.

26. The method of claim 24, wherein the step of providing the continuous low energy plasma discharge onto the ePTFE material, comprises:
providing a source of gas from which the plasma is generated, wherein the gas is selected from the group consisting of nitrogen, oxygen, argon and combinations thereof.

27. The method of claim 24, wherein power to generate the plasma discharge is from about 50 watts to about 500 watts.

28. The method of claim 24, further comprising:
providing the chamber with an operating pressure; and
reducing the operating pressure within the chamber to about 0.1 Pa to about 1.0 Pa.

29. The method of claim 24, further comprising:
oxidizing at least a portion of the free radials.

30. The method of claim 24, further comprising:
functionalizing the free radical sites with a spacer molecule or material, wherein the spacer molecule or material is covalently bonded to the modified ePTFE surface.

31. The method of claim 24, further comprising:
functionalizing the free radical sites with hydrophilic acrylamide groups.

32. The method of claim 31, further comprising:
covalently bonding the hydrophilic acrylamide groups to the modified ePTFE surface.

33. The method of claim 24, further comprising:
functionalizing the free radical sites with polysaccharide hydroxyethyl starch groups.

34. The method of claim 33, further comprising:
covalently bonding the polysaccharide hydroxyethyl starch groups to the modified ePTFE surface.

35. The method of claim 24, further comprising:
covalently bonding a bioactive agent bonded to the modified ePTFE surface.

36. The method of claim 32, further comprising:
covalently bonding a bioactive agent bonded to the hydrophilic acrylamide groups that are covalently bonded to the modified ePTFE surface.

37. The method of claim 34, further comprising:
covalently bonding a bioactive agent bonded to the polysaccharide hydroxyethyl starch groups that are covalently bonded to the modified ePTFE surface.

38. The method of claim 35, wherein the bioactive agent is selected from the group consisting of anti-thrombogenic agents, anti-proliferative agents, anti-inflammatory agents, antineoplastic/antiproliferative/anti-mitotic agents, anesthetic agents, anti-coagulants, vascular cell growth promotors, vascular cell growth inhibitors, cholesterol-lowering agents, vasodilating agents, agents which interfere with endogenous vasoactive mechanisms, cell adhesion factors; and combinations thereof.

39. The method of claim 24, wherein the ePTFE material is an implantable medical device.

40. The method of claim 39, wherein the implantable medical device is a vascular graft.

41. The method of claim 39, wherein the implantable medical device is a vascular stent-graft.

42. The method of claim 24, wherein the modified ePTFE surface has a depth of about 30 nm to about 500 nm.

* * * * *

UNITED STATES PATENT AND TRADEMARK OFFICE
CERTIFICATE OF CORRECTION

PATENT NO.       : 7,597,924 B2                                                                  Page 1 of 1
APPLICATION NO.  : 11/227378
DATED            : October 6, 2009
INVENTOR(S)      : Kondyurin et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 386 days Delete the phrase "by 386 days" and insert -- by 695 days --

Signed and Sealed this

Fourth Day of May, 2010

David J. Kappos
*Director of the United States Patent and Trademark Office*